United States Patent
Blaschuk et al.

(10) Patent No.: US 6,551,994 B1
(45) Date of Patent: *Apr. 22, 2003

(54) COMPOUNDS AND METHODS FOR INHIBITING THE INTERACTION BETWEEN α–CATENIN AND β–CATENIN

(75) Inventors: Orest W. Blaschuk, Westmount (CA); Barbara J. Gour, Montreal (CA)

(73) Assignee: McGill University, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/057,363

(22) Filed: Apr. 8, 1998

Related U.S. Application Data

(60) Provisional application No. 60/043,361, filed on Apr. 10, 1997.

(51) Int. Cl.[7] .................. A61K 38/08; A61K 38/10; A61K 38/12; C07K 7/08; C07K 7/54
(52) U.S. Cl. .................. 514/11; 530/317; 530/326; 530/327; 530/328; 530/329; 530/330; 514/13; 514/14; 514/15; 514/16; 514/17; 424/450
(58) Field of Search .................. 530/317, 300, 530/321, 324, 325, 326, 327, 328, 329, 330, 331; 514/9, 11, 2, 12, 13, 14, 15, 16, 17, 18; 424/450

(56) References Cited

U.S. PATENT DOCUMENTS

| 5,610,281 A | * | 3/1997 | Brenner | 530/388.85 |
| 5,922,855 A | * | 7/1999 | Liskay | 536/23.5 |
| 6,031,072 A | * | 2/2000 | Blaschuk | 530/317 |

FOREIGN PATENT DOCUMENTS

| WO | WO 91/04745 | 4/1991 |
| WO | WO 98/02452 | 1/1998 |
| WO | WO 98/45319 | 10/1998 |

OTHER PUBLICATIONS

Aberle et al., "Assembly of the cadherin–catenin complex in vitro with recombinant proteins," *Journal of Cell Science* 107: 3655–3663, 1994.

Blaschuk et al., "Identification of a Cadherin Cell Adhesion Recognition Sequence," *Developmental Biology* 139: 227–229, 1990.

Bullions and Levine, "The role of beta–catenin in cell adhesion, signal transduciton, and cancer," *Current Opinion in Oncology* 10: 81–87, 1998.

Jou et al., "Genetic and biochemical dissection of protein linkages in the cadherin–catenin complex," *Proc. Natl. Acad. Sci. USA* 92: 5067–5071, 1995.

Lutz et al., "Secondary Structure of the HAV Peptide Which Regulates Caherin–Cadherin Interaction," *Journal of Biomolecular Structure & Dynamics* 13(3): 447–455, 1995.

Su et al., "Association of the APC Tumor Suppressor Protein with Catenins," *Science* 262: 1734–1737, 1993.

Wheelock et al., "Membrane–Cytoskeleton Interactions with Cadherin Cell Adhesion Proteins: Roles of Catenins as Linker Proteins," *Current Topics in Membranes* 43: 169–185, 1996.

Willems et al., "Cadherin–dependent cell aggregation is affected by decapeptide derived from rat extracellular super-–oxide dismutase," *FEBS Letters 363*: 289–292, 1995.

* cited by examiner

*Primary Examiner*—Jeffrey E. Russel
(74) *Attorney, Agent, or Firm*—SEED Intellectual Property Law Group PLLC

(57) ABSTRACT

Modulating agents for inhibiting an interaction between α-catenin and β-catenin are provided. The modulating agents comprise one or more of: (a) a β-catenin HAV motif; (b) a peptide analogue or mimetic of a β-catenin HAV motif; or (c) an antibody or antigen-binding fragment thereof that specifically binds to a β-catenin HAV motif. Methods for using such modulating agents for inhibiting cadherin-mediated cell adhesion in a variety of contexts are also provided.

23 Claims, 6 Drawing Sheets

CHAVC

CKHAVC

CHAVVC

CKAVVC

CHAVVNC

CKHAVVNC

CLKHAVVNC

CLKHAVVC

CLKHAVC

KHAVVND

KHAVVNE

KHAVVD

KHAVVE

COMPOUNDS AND METHODS FOR INHIBITING THE INTERACTION BETWEEN α–CATENIN AND β–CATENIN

CROSS-REFERENCE TO RELATED APPLICATIONS

This application claims the benefit of U.S. Provisional Application No. 60/043,361, filed on Apr. 10, 1997.

TECHNICAL FIELD

The present invention relates generally to compounds and methods for use in inhibiting cadherin-mediated cell adhesion. The invention is more specifically related to modulating agents capable of inhibiting or disrupting interactions between catenin and β-catenin, and to therapeutic methods employing such agents.

BACKGROUND OF THE INVENTION

The ability of cells to recognize and bind to each other is a fundamental property of multicellular organisms. Such recognition and binding allows for the maintenance of tissue integrity and compartments, and prevents the inappropriate movement of cells and macromolecules between tissues. Cell adhesion also contributes to the natural adhesion of synapses in the body to prevent the remodeling of synapses. The molecules that are responsible for cellular recognition and binding are collectively known as cell adhesion molecules (CAMs).

There are many different families of CAMs, including the immunoglobulin, integrin, selectin and cadherin superfamilies, and each cell type expresses a unique combination of these molecules. Cadherins are a rapidly expanding family of calcium-dependent CAMs (see Munro et al., In. *Cell Adhesion and Invasion in Cancer Metastasis*, P. Brodt, ed., pp. 17–34, RG Landes Co. (Austin Tex., 1996)). Examples of the cadherin superfamily include N (neural)-cadherin, E (epithelial)-cadherin, P (placental)-cadherin, and R (retinal-cadherin). These cadherins (termed the classical cadherins, and abbreviated CADs) are integral membrane glycoproteins that generally promote cell adhesion through homophilic interactions (a CAD on the surface of one cell binds to an identical CAD on the surface of another cell), although CADs also appear to be capable of forming heterotypic complexes with one another under certain circumstances and with lower affinity. CADs have been shown to regulate epithelial, endothelial, neural and cancer cell adhesion, with different CADs expressed on different cell types. CADs also regulate the formation of intercellular junctions, and consequently the establishment of physical and permeability barriers between tissue compartments. If cadherin function is abrogated, such junctions between cells do not form.

The structures of the CADs are generally similar. As illustrated in FIG. 1, CADs are composed of five extracellular domains (EC1–EC5), a single hydrophobic domain (TM) that transverses the plasma membrane (PM), and two cytoplasmic domains (CP1 and CP2). The first extracellular domain (EC1) contains the classical cadherin cell adhesion recognition (CAR) sequence, HAV (His-Ala-Val), along with flanking sequences on either side of the CAR sequence that may play a role in conferring specificity.

Inside the cell, the second cytoplasmic domain (CP2) of the classical cadherins interacts with a cytoplasmic protein known as β-catenin (FIG. 1; designated as β) (see Wheelock et al., *Current Topics in Membranes* 43:169–185, 1996). This protein exists in a complex with another cytoplasmic protein, known as α-catenin (FIG. 1; designated as α). In the absence of this β-catenin/α-catenin complex, the classical cadherins cannot promote cell adhesion. α-catenin also binds to another cytoplasmic protein, known as α-actinin (FIG. 1; designated as ACT), which in turns interacts directly with actin-based microfilaments (FIG. 1; designated as MF) of the cytoskeleton.

β-Catenin is composed of 13 domains, referred to as arm repeats (FIG. 3; see Wheelock et al., *Current Topics in Membranes* 43:169–185, 1996). The arm repeat closest to the amino terminus of β-catenin (designated as the first arm repeat) is known to contain the α-catenin binding site. The specific amino acids that are directly involved in mediating the interaction between β-catenin and α-catenin have not previously been identified.

Although necessary for a variety of functions in multicellular organisms, CAM function (especially cadherin function) has been implicated in a range of pathological events, including the survival of cancer cells, the migration of cancer cells (metastasis) and the vascularization of tumors (angiogenesis). In such circumstances, it would be advantageous to modulate cadherin function. In order to develop effective therapeutic agents that modulate cadherin function, it is important to further understand the mechanism of cadherin-mediated cell adhesion.

Accordingly, there is a need in the art for improved methods for modulating cadherin function. The present invention fulfills this need and further provides other related advantages.

SUMMARY OF THE INVENTION

The present invention provides methods for modulating cadherin-mediated functions. Within certain aspects, the present invention provides modulating agents capable of inhibiting an interaction between α-catenin and β-catenin. In one such aspect, the modulating agent comprises one or more of: (a) the amino acid sequence KHAVV (SEQ ID NO:1); (b) a peptide analogue or peptidomimetic of the amino acid sequence KHAVV (SEQ ID NO:1); or (c) an antibody or antigen-binding fragment thereof that specifically binds to a peptide comprising the amino acid sequence KHAVV (SEQ ID NO:1). Within certain embodiments, the modulating agent comprises the sequence KHAVV (SEQ ID NO:1) within a linear peptide or a cyclic peptide ring. Such modulating agents may, within certain embodiments, comprise a linear or cyclic peptide ranging from 3 to 16 amino acid residues in length.

In another such aspect, a modulating agent comprises: (a) the amino acid sequence HAV; (b) a peptide analogue or peptidomimetic of the amino acid sequence HAV; or (c) an antibody or antigen-binding fragment thereof that specifically binds to a peptide comprising the amino acid sequence HAV; wherein the modulating agent is associated with an internalization moiety. In certain embodiments, the modulating agent comprises a linear or cyclic peptide sequence, which may range from 3 to 16 amino acid residues in length. The internalization moiety may comprise, within certain embodiments, an internalization sequence covalently linked to the modulating agent, a liposome that encapsulates the modulating agent or an antibody or ligand that binds to a cell surface receptor.

Within further embodiments, any of the above modulating agents may be linked to a targeting agent and/or a drug.

Within other aspects, the present invention provides pharmaceutical compositions comprising a cell adhesion modulating agent as described above, in combination with a pharmaceutically acceptable carrier.

The present invention further provides, within other aspects, methods for disrupting an interaction between α-catenin and β-catenin in a cell, comprising contacting a cell with a cell adhesion modulating agent as described above.

Within further related aspects, the present invention provides methods for inhibiting cellular adhesion, comprising contacting a cadherin-expressing cell with a cell adhesion modulating agent as described above.

In other aspects, methods are provided for treating a demyelinating neurological disease in a mammal, comprising administering to a mammal a modulating agent as described above. The modulating agent may be administered, within certain embodiments, by implantation with Schwann cells or by implantation with oligodendrocyte progenitor cells and/or oligodendrocytes.

The present invention further provides, within other aspects, methods for reducing unwanted cellular adhesion in a mammal, comprising administering to a mammal a modulating agent as described above.

Within further aspects, methods are provided for enhancing the delivery of a drug through the skin of a mammal, comprising contacting epithelial cells of a mammal with a drug and a modulating agent as described above, wherein the step of contacting is performed under conditions and for a time sufficient to allow passage of the drug across the epithelial cells. In certain embodiments, the modulating agent passes into the blood stream of the mammal. The modulating agent may be linked to the drug and/or the step of contacting may be performed via a skin patch comprising the modulating agent and the drug.

In other aspects, methods are provided for enhancing the delivery of a drug to a tumor in a mammal, comprising administering to a mammal a modulating agent as described above. The modulating agent may be administered to the tumor or may be administered systemically.

Within related aspects, the present invention provides methods for treating cancer in a mammal, comprising administering to a mammal a modulating agent as described above.

The present invention further provides, within other aspects, methods for inhibiting angiogenesis in a mammal, comprising administering to a mammal a modulating agent as described above.

Within further aspects, the present invention provides methods for enhancing drug delivery to the central nervous system of a mammal, comprising administering to a mammal a modulating agent as described above.

Within other aspects, the present invention provides methods for inducing apoptosis in a cadherin-expressing cell, comprising contacting a cadherin-expressing cell with a modulating agent as described above.

Within further aspects, methods are provided for modulating the immune system of a mammal, comprising administering to a mammal a modulating agent as described above.

The present invention further provides, within other aspects, methods for preventing pregnancy in a mammal, comprising administering to a mammal a modulating agent as described above.

Within other aspects, the present invention provides methods for increasing vasopermeability in a mammal, comprising administering to a mammal a modulating agent as described above.

In further aspects, methods are provided for inhibiting synaptic stability in a mammal, comprising administering to a mammal a modulating agent as described above.

Within further aspects, the present invention provides kits for enhancing transdermal drug delivery, comprising: (a) a skin patch; and (b) a modulating agent as described above. The skin patch may be impregnated with the modulating agent and/or may further comprise a drug.

The present invention further provides polynucleotides encoding a modulating agent as described above. Such polynucleotides may be incorporated into a viral vector, such that the modulating agent is generated within a cell infected by the viral vector.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 4 illustrates the local alignment of classical cadherins with β-catenins (SEQ ID NOs:52–71).

FIG. 6 is a Western blot as shown in FIG. 5, re-probed with anti-β-cantenin antibodies.

DETAILED DESCRIPTION OF THE INVENTION

Figure 1:
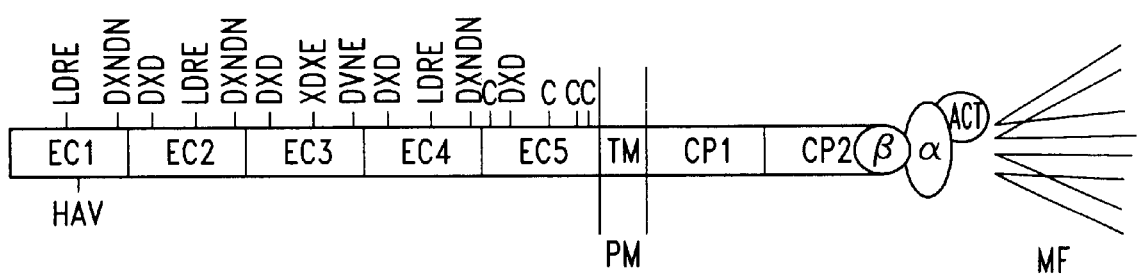
FIG. 1 is a schematic diagram showing the structure of a classical cadherin and its interaction with the catenins. The five extracellular domains are designated EC1–EC5, the hydrophobic domain that transverses the plasma membrane (PM) is represented by TM, and the two cytoplasmic domains are represented by CP1 and CP2. The calcium binding motifs are shown by DXNDN (SEQ ID NO:2), DXD, LDRE (SEQ ID NO:3) and DVNE (SEQ ID NO:72). The CAR sequence, HAV, is shown within EC1. Cytoplasmic proteins β-catenin (β), α-catenin (α) and α-actinin (ACT), as well as microfilaments (MF), are also shown.
Figure 2A:
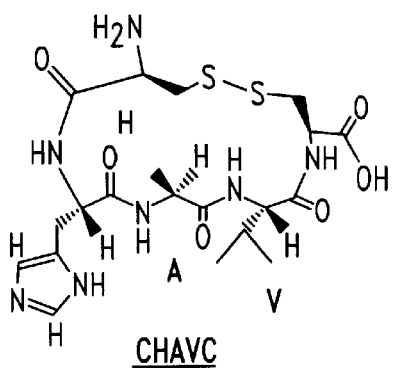
FIGS. 2A–2C illustrate the structures of the following representative cyclic peptide modulating agents: CHAVC (SEQ ID NO:34), CKHAVC (SEQ ID NO:31), CHAVVC (SEQ ID NO:33), CKAVVC (SEQ ID NO:73), CHAVVNC (SEQ ID NO:32), CKHAVVNC (SEQ ID NO:5), CLKHAVVNC (SEQ ID NO:23), CLKHAVVC (SEQ ID NO:24), CLKHAVC (SEQ ID NO:30), KHAVVND (SEQ ID NO:26), KHAVVNE (SEQ ID NO:27), KHAVVD (SEQ ID NO:28), and KHAVVE (SEQ ID NO:29).
Figure 2A:
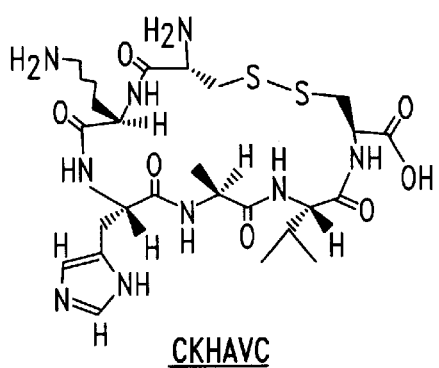
Figure 2A:
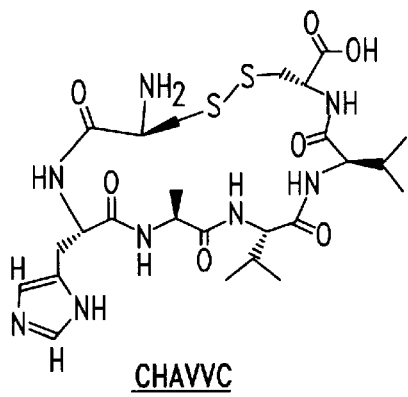
Figure 2A:
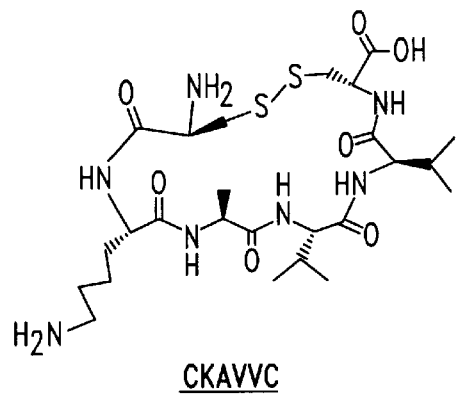
Figure 2A:
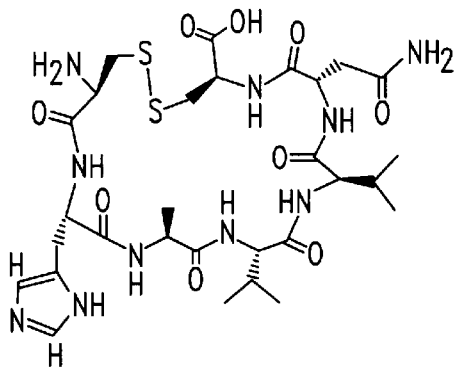
Figure 2A:
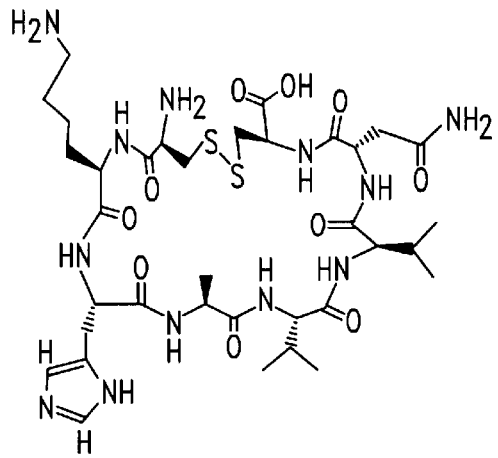
Figure 2B:
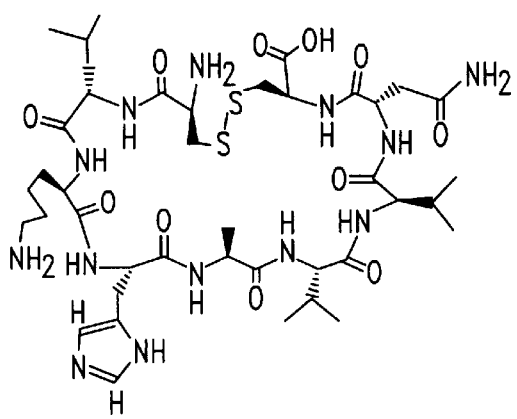
Figure 2B:
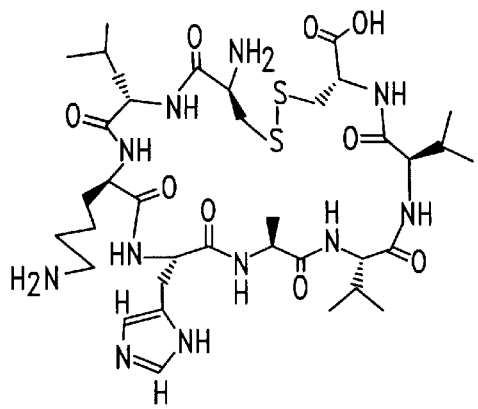
Figure 2B:
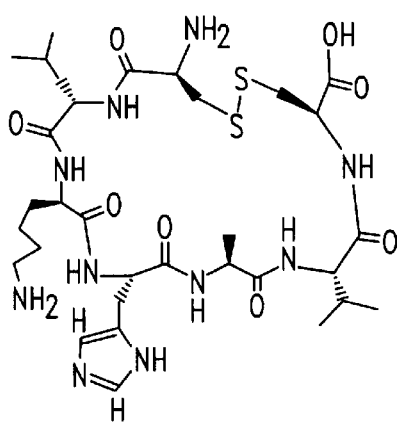
Figure 2B:
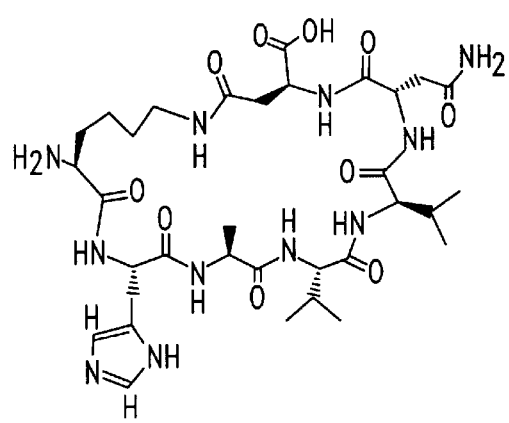
Figure 2B:
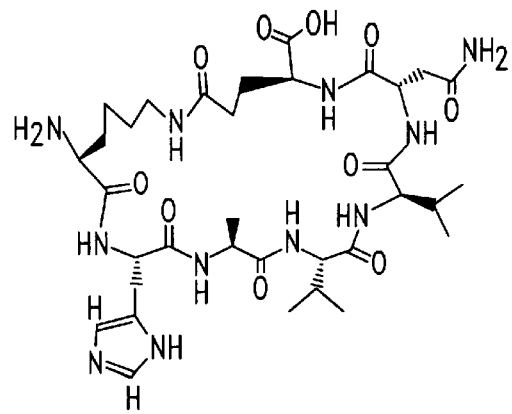
Figure 2B:
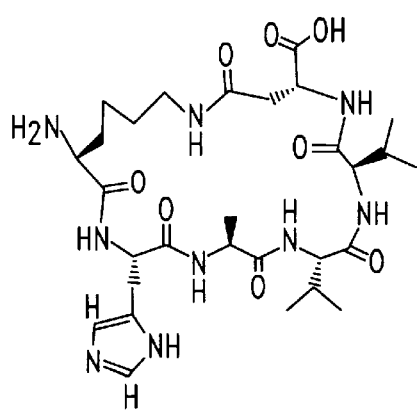
Figure 2C:
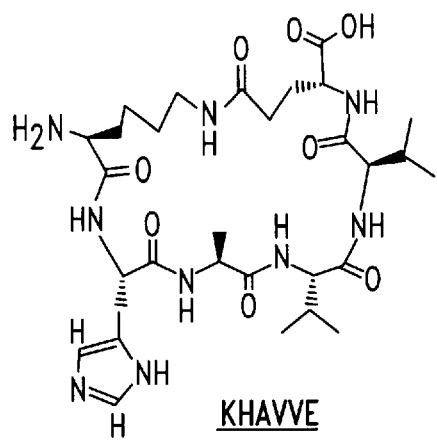
Figure 3:
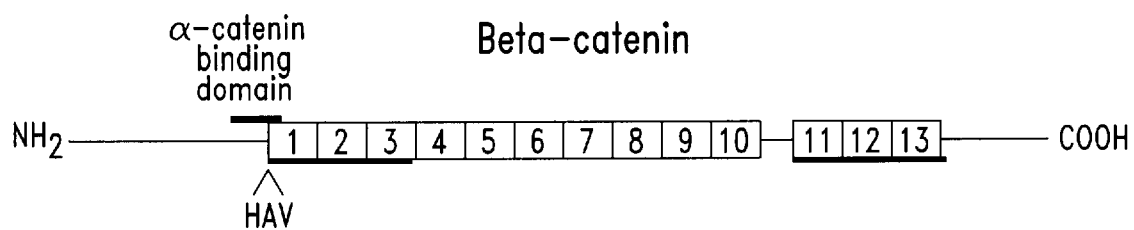
FIG. 3 is a diagram showing the structure of β-catenin.

As noted above, the present invention provides methods for inhibiting cadherin-mediated cell adhesion. The present invention is based upon the identification of an HAV motif within the first arm repeat of β-catenin (see FIG. 3) and the discovery that HAV-containing peptides are capable of disrupting interactions between α-catenin and β-catenin. Modulating agents that comprise such peptides or antibodies directed against such peptides may be used to inhibit cadherin-mediated cell adhesion within a variety of contexts. For example, such agents may be used to treat diseases or other conditions characterized by undesirable cell adhesion, to facilitate drug delivery to a specific tissue or tumor or to inhibit angiogenesis.

Modulating Agents

As noted above, the term "modulating agent," as used herein, refers to a molecule comprising one or more of (1) a β-catenin HAV motif, (2) a peptide analogue or peptidomimetic thereof or (3) an antibody or antigen-binding fragment thereof that specifically binds to such a motif. A modulating agent is further capable of disrupting interactions between α-catenin and β-catenin, as described herein.

Figure 4:
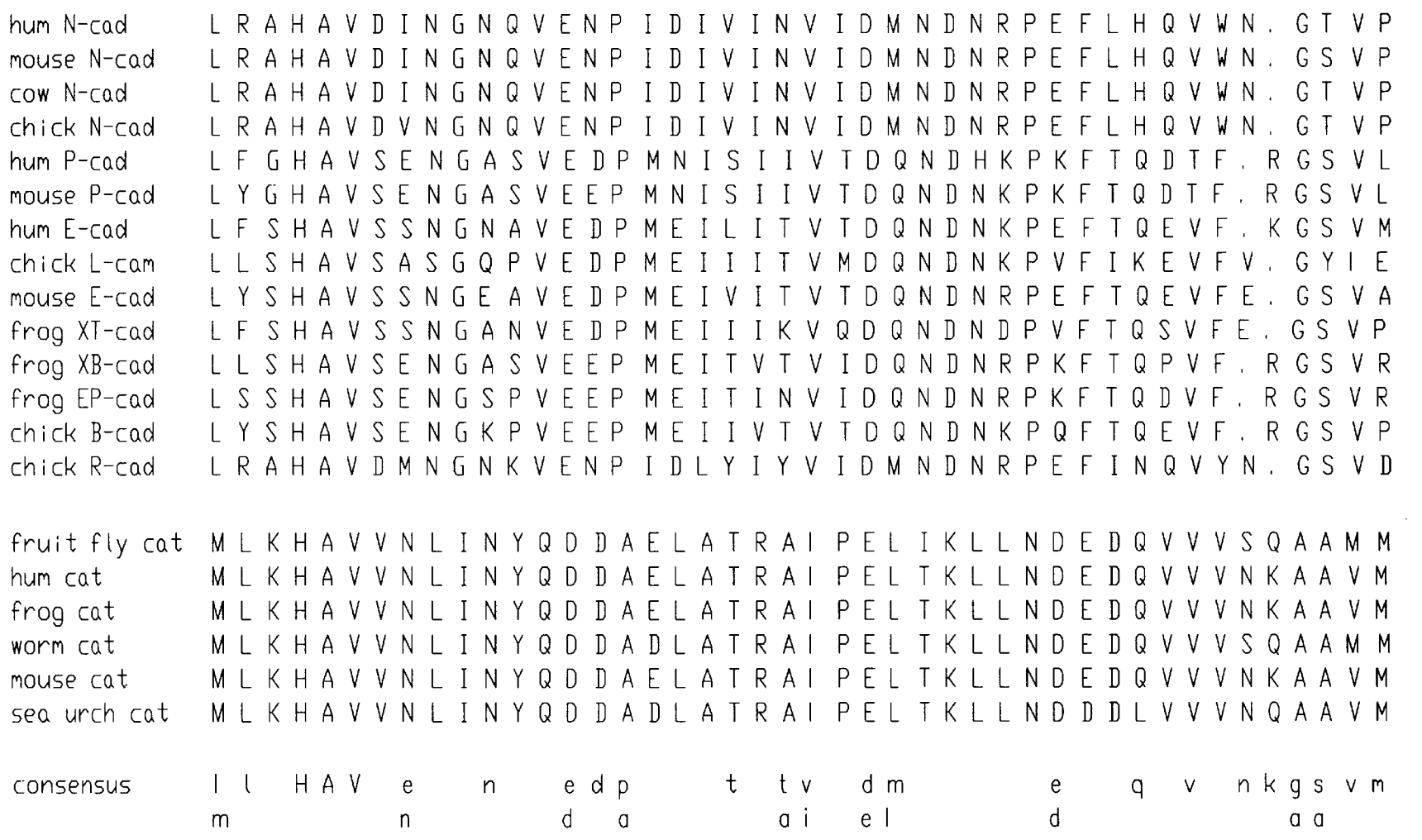

As used herein, a "β-catenin HAV motif" comprises the tripeptide sequence HAV. Within certain preferred embodiments, the β-catenin HAV motif further comprises at least one, and more preferably at least two or three, amino acid residues that flank the HAV sequence in a native β-catenin molecule (i.e., residues that are adjacent to the HAV sequence located within the first arm repeat of a native β-catenin molecule). Flanking sequences for β-catenin of a variety of organisms are shown in SEQ ID NOs:52 to 71, and FIG. 4. Flanking sequences are preferably derived from the sequence LKHAVVNLIN (SEQ ID NO:7). Flanking residue(s) may be present on the N-terminal and/or C-terminal side of an HAV motif, preferably on both sides. Within certain preferred embodiments, a modulating agent comprises the β-catenin HAV motif KHAVV (SEQ ID NO:1). A modulating agent may consist entirely of a β-catenin HAV motif, or may additionally comprise further peptide and/or non-peptide regions, such as regions that facilitate cyclization, purification or other manipulation and/or residues having a targeting or other function. Modulating agents may further be associated (covalently or noncovalently) with an internalization moiety, targeting agent, drug, solid support and/or detectable marker.

Modulating agents, or peptide portions thereof, may be linear or cyclic peptides. A "linear" peptide is a peptide or salt thereof that does not contain an intramolecular covalent bond between two non-adjacent residues. Within preferred embodiments, linear peptide modulating agents typically comprise from 5 to about 20 amino acid residues, preferably from 5 to 16 amino acid residues and more preferably from 5 to 10 amino acid residues. Linear peptides that may be present within a modulating agent include, but are not limited to, KHAVVN (SEQ ID NO:8), LKHAVVN (SEQ ID NO:9), LKHAVV (SEQ ID NO:10), LKHAV (SEQ ID NO:11), KHAVV (SEQ ID NO:1), CKHAVVNC (SEQ ID NO:4), CLKHAVVNC (SEQ ID NO:12), CLKHAVVC (SEQ ID NO:13), CLKHAVC (SEQ ID NO:14), CKHAVVC (SEQ ID NO:15), KHAV (SEQ ID NO:16), HAVVN (SEQ ID NO:17), HAVN (SEQ ID NO:18), HAV, CKHAVC (SEQ ID NO:19), CHAVVNC (SEQ ID NO:20), CHAVVC (SEQ ID NO:21) and CHAVC (SEQ ID NO:22), as well as derivatives of the foregoing sequences having one or more side chain modifications.

The term "cyclic peptide," as used herein, refers to a peptide or salt thereof that comprises an intramolecular covalent bond between two non-adjacent residues, forming a cyclic peptide ring that comprises the β-catenin HAV motif, or analogue thereof. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide bonds; amide bonds between terminal functional groups, between residue side chains or between one terminal functional groups and one residue side chain; thioether bonds and $\delta_1,\delta_1$-ditryptophan or a derivative thereof. Preferred cyclic peptide modulating agents generally comprise from 4 to 15 residues, more preferably from 5 to 10 residues, within the cyclic peptide ring. Preferred cyclic peptides include C<u>KHAVVN</u>C (SEQ ID NO:5), C<u>LKHAVVN</u>C (SEQ ID NO:23), C<u>LKHAVV</u>C (SEQ ID NO:24), C<u>KHAVV</u>C (SEQ ID NO:25), <u>KHAVVN</u>D (SEQ ID NO:26), <u>KHAVVN</u>E (SEQ ID NO:27), <u>KHAVV</u>D (SEQ ID NO:28), <u>KHAVV</u>E (SEQ ID NO:29), C<u>LKHAV</u>C (SEQ ID NO:30), C<u>KHAV</u>C (SEQ ID NO:31), C<u>HAVVN</u>C (SEQ ID NO:32), C<u>HAVV</u>C (SEQ ID NO:33), C<u>HAV</u>C (SEQ ID NO:34), <u>KHAV</u>D (SEQ ID NO:35) and <u>KHAV</u>E (SEQ ID NO:36), where the underline indicates cyclization, as well as derivatives of the foregoing sequences having one or more side chain modifications.

As noted above, modulating agents may be polypeptides or salts thereof, containing only amino acid residues linked by peptide bonds, or may additionally contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations shown in Table 1.

TABLE 1

| Amino acid one-letter and three-letter abbreviations | | |
|---|---|---|
| A | Ala | Alanine |
| R | Arg | Arginine |
| D | Asp | Aspartic acid |
| N | Asn | Asparagine |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

As noted above, a modulating agent may comprise a peptide analogue or a non-peptide peptidomimetic of a native β-catenin HAV motif, provided that the analogue or peptidomimetic retains the ability to disrupt an interaction between α-catenin and β-catenin. In general, a peptide analogue of a native β-catenin sequence should retain the HAV sequence, but may contain conservative substitutions at one or more flanking residues such that the ability to disrupt interactions between α-catenin and β-catenin is not diminished. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. The critical determining feature of a peptide analogue is the ability to disrupt an interaction between α- and β-catenin. Such an ability may be evaluated using the representative assays provided herein.

A peptidomimetic is a non-peptide compound that is structurally similar to a β-catenin HAV motif, such that it retains the ability to disrupt interactions between α-catenin and β-catenin, as described below. Peptidomimetics are organic compounds that mimic the three-dimensional shape of a β-catenin HAV motif. Peptidomimetics may be designed based on techniques that evaluate the three dimensional shape, such as nuclear magnetic resonance (NMR) and computational techniques. NMR is widely used for structural analysis of molecules. Cross-peak intensities in nuclear Overhauser enhancement (NOE) spectra, coupling constants and chemical shifts depend on the conformation of a compound. NOE data provide the interproton distance between protons through space. This information may be used to facilitate calculation of the lowest energy conformation for the HAV motif. Once the lowest energy conformation is known, the three-dimensional shape to be mimicked is known. It should be understood that, within embodiments described herein, an analogue or peptidomimetic may be substituted for a native HAV motif.

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using solution phase or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation may be accomplished using an appropriate resin such as methylbenzhydrylamine resin using the Boc technology.

Following synthesis of a linear peptide, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized, N-acetyl groups are indicated by N-Ac and C-terminal amide groups are represented by —$NH_2$:

| | | | |
|---|---|---|---|
| i) | H-<u>Lys-His-Ala-Val-Val-Asn</u>-OH | (SEQ ID NO:37) |
| ii) | H-<u>Leu-Lys-His-Ala-Val-Val-Asn</u>-OH | (SEQ ID NO:38) |
| iii) | H-<u>His-Ala-Val-Val-Asn</u>-OH | (SEQ ID NO:39) |
| iv) | H-<u>His-Ala-Val-Val</u>-OH | (SEQ ID NO:40) |
| v) | H-<u>Cys-Lys-His-Ala-Val-Val-Asn-Cys</u>-OH | (SEQ ID NO:5) |
| vi) | H-<u>Cys-Leu-Lys-His-Ala-Val-Val-Asn-Cys</u>-OH | (SEQ ID NO:23) |
| vii) | H-<u>Cys-His-Ala-Val-Val-Asn-Cys</u>-OH | (SEQ ID NO:32) |
| viii) | H-<u>Cys-His-Ala-Val-Val-Cys</u>-OH | (SEQ ID NO:33) |
| ix) | H-<u>Cys-Lys-His-Ala-Val-Val-Asn-Pen</u>-OH | (SEQ ID NO:41) |
| x) | H-<u>Tmc-Lys-His-Ala-Val-Val-Asn-Cys</u>-OH | (SEQ ID NO:42) |
| xi) | H-<u>Pmc-Lys-His-Ala-Val-Val-Asn-Cys</u>-OH | (SEQ ID NO:43) |
| xii) | H-<u>Mpr-Lys-His-Ala-Val-Val-Asn-Cys</u>-OH | (SEQ ID NO:44) |
| xiii) | H-<u>Pmp-Lys-His-Ala-Val-Val-Asn-Cys</u>-OH | (SEQ ID NO:45) |

It will be readily apparent to those of ordinary skill in the art that, within each of these representative formulas, any of the above thiol-containing residues may be employed in place of one or both of the thiol-containing residues recited.

Within another embodiment, cyclization may be achieved by amide bond formation. For example, a peptide bond may be formed between terminal functional groups (i.e., the amino and carboxy termini of a linear peptide prior to cyclization), with or without an N-terminal acetyl group and/or a C-terminal amide. Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and arc based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

i.

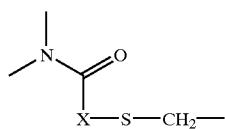

X = (CH$_2$)$_4$
 = CH$_2$

ii.

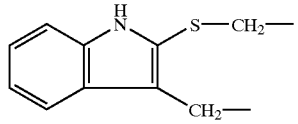

Cyclization may also be achieved using δ$_1$,δ$_1$'-Ditryptophan (i.e., Ac-<u>Trp-Gly-Gly-Trp</u>-OMe) (SEQ ID NO:46), as shown below:

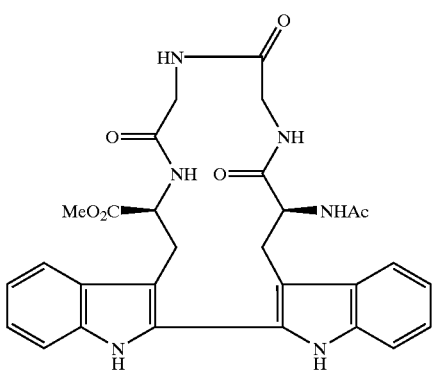

Representative cyclic peptide modulating agents are depicted in FIG. 2. The structures and formulas recited herein are provided solely for the purpose of illustration, and are not intended to limit the scope of the modulating agents described herein.

For longer peptide modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous β-catenin and/or other sequences. Endogenous β-catenin sequences may be prepared based on known cDNA or genomic sequences (see Wheelock et al., *Current Topics in Membranes* 43:169–185, 1996), which may be isolated by screening an appropriate library with probes designed based on such known sequences. Screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous β-catenin. To generate a nucleic acid molecule encoding a desired modulating agent, an endogenous β-catenin sequence may be modified using well known techniques. For example, portions encoding one or more HAV motifs may be joined, with or without separation by unrelated nucleic acid regions. Alternatively, portions of the desired nucleic acid sequences may be synthesized using well known techniques, and then ligated together to form a sequence encoding the modulating agent.

As noted above, a modulating agent may comprise an antibody, or antigen-binding fragment thereof, that specifically binds to a β-catenin HAV motif. As used herein, an antibody, or antigen-binding fragment thereof, is said to "specifically bind" to such a motif if it reacts at a detectable level (within, for example, an ELISA) with a peptide containing the motif, and does not react detectably with peptides that do not contain a β-catenin HAV motif.

Antibodies and fragments thereof may be prepared using standard techniques. See, e.g., Harlow and Lane, *Antibodies: A Laboratory Manual*, Cold Spring Harbor Laboratory, 1988. In one such technique, an immunogen comprising a β-catenin HAV motif is initially injected into any of a wide variety of mammals (e.g., mice, rats, rabbits, sheep or goats). Small immunogens (i.e., less than about 20 amino acids)

should be joined to a carrier protein, such as bovine serum albumin or keyhole limpet hemocyanin. Following one or more injections, the animals are bled periodically. Polyclonal antibodies specific for the β-catenin HAV motif may then be purified from such antisera by, for example, affinity chromatography using the modulating agent or antigenic portion thereof coupled to a suitable solid support.

Monoclonal antibodies specific for a β-catenin HAV motif may be prepared, for example, using the technique of Kohler and Milstein, Eur. J. Immunol. 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred. To evaluate the specificity of a particular antibody, conventional antigen-binding assays may be employed.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target catenin is localized.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

Within certain embodiments, it may be beneficial to employ modulating agents that are associated with an internalization moiety. An internalization moiety is any moiety (such as a compound, liposome or particle) that can be used to improve the ability of an agent to penetrate the lipid bilayer of the cellular plasma membrane, thus enabling the agent to readily enter the cytoplasm and disrupt interactions between cytosolic α-catenin and β-catenin. As used herein, the term "associated with" refers to covalent attachment or a non-covalent interaction mediated by, for example, ionic bonds, hydrogen bonds, van der waals forces and/or hydrophobic interactions, such that the internalization moiety and modulating agent remain in close proximity under physiological conditions.

Within certain embodiments, an internalization moiety is an internalization sequence. An internalization sequence may be any sequence (generally a peptide sequence) that is capable of facilitating entry of the modulating agent into the cytosol of a living cell. One suitable internalization sequence is a 16 amino acid peptide derived from the third helix of the Antennapedia protein, and having the sequence RQIKIWFQNRRMKWKK (SEQ ID NO:47; see Prochiantz, Curr. Op. Neurobiol. 6:629–34, 1996) or RQIKIWPQNRRNKWKK (SEQ ID NO:48). Analogues of this sequence (i.e., sequences having at least 25% sequence identity, such that the ability to facilitate entry into the cytosol is not diminished) may also be employed. One such analogue is KKWKKWWKKWWKKWKK (SEQ ID NO:49). One preferred modulating agent associated with an Antennapedia internalization sequence has the sequence KHAVVNRQIKIWFQNRRMKWKK (SEQ ID NO:50).

Alternatively, an internalization sequence may be unrelated to the Antennapedia sequence. In general, the ability of a sequence to facilitate entry into the cytosol may be evaluated by covalently linking such a sequence to a known modulating agent and evaluating the ability of the modulating agent to disrupt interactions between α-catenin and β-catenin, as described herein. Within such an assay, an internalization sequence should permit a level of disruption that is statistically greater than that observed in the absence of internalization sequence. Preferably, an internalization sequence incorporated into a modulating agent results in a level of disruption that is comparable to, or greater than, that observed for the modulating agent comprising an internalization sequence derived from Antennapedia.

An internalization sequence may be covalently linked to a modulating agent. Such linkage may be generated using any of a variety of means well known in the art, either directly or by way of a spacer. In general, spacers may be amino acid residues (e.g., amino hexanoic acid) or peptides, or may be other bi- or multi-functional compounds that can be covalently linked to at least two peptide sequences. Covalent linkage may be achieved via direct condensation or other well known techniques.

Other internalization moieties may also be employed. In general, any moiety that permits a level of disruption that is statistically greater than that observed in its absence is considered an internalization moiety. Preferably, an internalization moiety results in a level of disruption that is comparable to, or greater than, that observed for the modulating agent associated with an internalization sequence derived from Antennapedia, as described above. For example, a modulating agent may be incorporated into a liposome (i.e., an artificial membrane vesicle), using well known technology. Other internalization moieties include, but are not limited to, antibodies and ligands that bind to cell surface receptors. Alternatively, a polynucleotide encoding a modulating agent may be incorporated into an appropriate viral vector, such that the modulating agent is generated within the target cell. Various particle-mediated delivery systems are also available, and their use is well known to those of ordinary skill in the art.

Evaluation of Modulating Agent Activity

As noted above, modulating agents are capable of disrupting an interaction between α-catenin and β-catenin. This ability may generally be evaluated using any suitable assay known to those of ordinary skill in the art. For example, an immunoprecipitation as described herein may be employed. Within such an assay, disruption of the interaction is measured by assessing the ability of an antibody directed against β-catenin to immunoprecipitate α-catenin in the presence and absence of the modulating agent. For example, tissue such as brain may be homogenized in the presence and absence of modulating agent. The ability of an antibody directed against β-catenin to immunoprecipitate α-catenin from the homogenate is then assessed by probing a Western blot of proteins immunoprecipitated from the tissue homogenate by anti-β-catenin antibody with an anti-α-catenin antibody. The resulting signal is indicative of the level of interaction between α-catenin and β-catenin. In general, a modulating agent should inhibit such interaction by at least 50%.

Modulating agents also inhibit cadherin-mediated cell adhesion. This property may be evaluated using any of a variety of in vitro assays designed to measure the effect of the peptide on a typical cadherin response. The ability of an agent to modulate cell adhesion may generally be evaluated in vitro by assaying the effect on one or more of the following: (1) neurite outgrowth, (2) Schwann cell-astrocyte adhesion, (3) Schwann cell migration on astrocyte monolayers, (4) adhesion between endothelial cells, (5) adhesion between epithelial cells (e.g., normal rat kidney cells and/or human skin) and/or (6) adhesion between cancer cells. In general, a modulating agent is an inhibitor of cell adhesion if, within one or more of these representative assays, contact of the test cells with the modulating agent results in a discernible disruption of cell adhesion.

Within a representative neurite outgrowth assay, neurons may be cultured on a monolayer of cells (e.g., 3T3 fibroblasts) that express N-cadherin. Neurons grown on such cells (under suitable conditions and for a sufficient period of time) extend neurites that are typically, on average, twice as long as neurites extended from neurons cultured on 3T3 cells that do not express N-cadherin. For example, neurons may be cultured on monolayers of 3T3 cells transfected with cDNA encoding N-cadherin essentially as described by Doherty and Walsh, *Curr. Op. Neurobiol* 4:49–55, 1994; Williams et al., *Neuron* 13:583–594, 1994; Hall et al., *Cell Adhesion and Commun.* 3:441–450, 1996; Doherty and Walsh, *Mol Cell. Neurosci.* 8:99–111, 1994; and Safell et al., Neuron 18:231–242, 1997. Briefly, monolayers of control 3T3 fibroblasts and 3T3 fibroblasts that express N-cadherin may be established by overnight culture of 80,000 cells in individual wells of an 8-chamber well tissue culture slide. 3000 cerebellar neurons isolated from post-natal day 3 mouse brains may be cultured for 18 hours on the various monolayers in control media (SATO/2%FCS), or media supplemented with various concentrations of the modulating agent or control peptide. The cultures may then be fixed and stained for GAP43 which specifically binds to the neurons and their neurites. The length of the longest neurite on each GAP43 positive neuron may be measured by computer assisted morphometry. Under the conditions described above, the presence of 500 $\mu$g/mL of a modulating agent should result in a decrease in the mean neurite length by at least 50%, relative to the length in the absence of modulating agent or in the presence of a negative control peptide.

The effect of a modulating agent on Schwann cell adhesion to astrocytes may generally be evaluated using a cell adhesion assay. Briefly, Schwann cells fluorescently labeled with Di-I may be plated onto an astrocytic surface (e.g., a glass coverslip coated with a monolayer of astrocytes) and incubated on a shaking platform (e.g., 25 rpm for 30 minutes) in the presence and absence of modulating agent at a concentration of approximately 1 mg/mL. Cells may then be washed (e.g., in Hanks medium) to remove non-attached cells. The attached cells may then be fixed and counted (e.g., using a fluorescent microscope). In general, 1 mg/mL of a modulating agent results in a decrease in cell adhesion of at least 50%. This assay evaluates the effect of a modulating agent on N-cadherin mediated cell adhesion.

Schwann cell migration may generally be evaluated using a micro-inverted-coverslip assay. In this assay, a dense Schwann cell culture is established on coverslip fragments and Schwann cell migration away from the fragment edge is measured. Briefly, Schwann cells fluorescently labeled with Di-I may be plated on polylysine- and laminin-coated fragments of a glass coverslip and allowed to bind to the surface for 16–18 hours. Cells may then be washed (e.g., in Hanks medium) to remove non-attached cells, and then inverted, with cells facing downward onto an astrocyte-coated surface. Cultures are then incubated further for 2 days in the presence or absence of modulating agent at a concentration of approximately 1 mg/mL and fixed. The maximum migration distance from the edge of the coverslip fragment may then be measured. At a level of 1 mg/mL, a modulating agent results in a decrease in the maximum migration distance of at least 50%. This assay evaluates the effect of a modulating agent on N-cadherin mediated cell adhesion.

In general, the addition of a modulating agent to cells that express a cadherin results in disruption of cell adhesion. A "cadherin-expressing cell," as used herein, may be any type of cell that expresses at least one cadherin on the cell surface at a detectable level, using standard techniques such as immunocytochemical protocols (e.g., Blaschuk and Farookhi, *Dev. Biol.* 136:564–567, 1989). Cadherin-expressing cells include endothelial, epithelial and/or cancer cells. For example, such cells may be plated under standard conditions that, in the absence of modulating agent, permit cell adhesion. In the presence of modulating agent (e.g., 500 $\mu$g/mL), disruption of cell adhesion may be determined visually within 24 hours, by observing retraction of the cells from one another.

For use within one such assay, bovine pulmonary artery endothelial cells may be harvested by sterile ablation and digestion in 0.1% collagenase (type II; Worthington Enzymes, Freehold, N.J.). Cells may be maintained in Dulbecco's minimum essential medium supplemented with 10% fetal calf serum and 1% antibiotic-antimycotic at 37° C. in 7% $CO_2$ in air. Cultures may be passaged weekly in trypsin-EDTA and seeded onto tissue culture plastic at 20,000 cells/cm$^2$. Endothelial cultures may be used at 1 week in culture, which is approximately 3 days after culture confluency is established. The cells may be seeded onto coverslips and treated (e.g., for 30 minutes) with modulating agent or a control compound at, for example, 500 $\mu$g/ml and then fixed with 1% paraformaldehyde. As noted above, disruption of cell adhesion may be determined visually within 24 hours, by observing retraction of the cells from one another. This assay evaluates the effect of a modulating agent on N-cadherin mediated cell adhesion.

Within another such assay, the effect of a modulating agent on normal rat kidney (NRK) cells may be evaluated. According to a representative procedure, NRK cells (ATCC #1571-CRL) may be plated at 10–20,000 cells per 35 mm tissue culture flasks containing DMEM with 10% FCS and sub-cultured periodically (Laird et al., *J. Cell Biol.* 131:1193–1203, 1995). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 100% methanol for 10 minutes and then washed three times with PBS. Coverslips may be blocked for 1 hour in 2% BSA/PBS and incubated for a further 1 hour in the presence of mouse anti-E-cadherin antibody (Transduction Labs, 1:250 dilution). Primary and secondary antibodies may be diluted in 2% BSA/PBS. Following incubation in the primary antibody, coverslips may be washed three times for 5 minutes each in PBS and incubated for 1 hour with donkey anti-mouse antibody conjugated to fluorescein (diluted 1:200). Following further washes in PBS (3×5 min) coverslips can be mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts E-cadherin mediated cell adhesion may assume a non-polygonal and elongated morphology (i.e., a fibroblast-like shape) within 48 hours of treatment with 1 mg/mL of modulating agent. Gaps appear in confluent cultures of such cells. In addition. 1 mg/mL of such a modulating agent reproducibly induces a readily apparent reduction in cell surface staining of E-cadherin, as judged by immunofluorescence microscopy (Laird et al., *J. Cell Biol.* 131:1193–1203, 1995), of at least 75% within 48 hours.

A third cell adhesion assay involves evaluating the effect of a modulating agent on permeability of adherent epithelial and/or endothelial cell layers. For example, the effect of permeability on human skin may be evaluated. Such skin may be derived from a natural source or may be synthetic. Human abdominal skin for use in such assays may generally be obtained from humans at autopsy within 24 hours of death. Briefly, a modulating agent (e.g., 500 μg/ml) and a test marker (e.g., the fluorescent markers Oregon Green™ and Rhodamine Green™ Dextran) may be dissolved in a sterile buffer (e.g., phosphate buffer, pH 7.2), and the ability of the marker to penetrate through the skin and into a receptor fluid (e.g., phosphate buffer) may be measured using a Franz Cell apparatus (Franz, *Curr. Prob. Dermatol.* 7:58–68, 1978; Franz, J. Invest. Dermatol. 64:190–195, 1975). The penetration of the markers through the skin may be assessed at, for example, 6, 12, 24, 36, and 48 hours after the start of the experiment. In general, a modulating agent results in a statistically significant increase in the amount of marker in the receptor compartment after 6–48 hours in the presence of 500 μg/mL modulating agent. This assay evaluates the effect of a modulating agent on E-cadherin mediated cell adhesion.

Modulating Agent Modification and Formulations

A modulating agent as described herein may, but need not, be linked to one or more additional molecules. Although modulating agents as described herein may preferentially bind to specific tissues or cells, and thus may be sufficient to target a desired site in vivo, it may be beneficial for certain applications to include an additional targeting agent. Accordingly, a targeting agent may be associated with a modulating agent to facilitate targeting to one or more specific tissues. As used herein, a "targeting agent," may be any substance (such as a compound or cell) that, when associated with a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.002%. Fluid compositions typically contain about 10 ng/ml to 5 mg/ml, preferably from about 10 μg to 2 mg/mL modulating agent. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating the adhesion of cadherin-expressing cells (i.e., cells that express one or more of E-cadherin, N-cadherin, P-cadherin, R-cadherin and/or other cadherins, which may be known or as yet undiscovered). Such modulation may be performed in vitro and/or in vivo, preferably in a mammal such as a human.

Certain methods described herein have an advantage over prior techniques in that they permit the passage of molecules that are large and/or charged across barriers of cadherin-expressing cells. As described in greater detail below, modulating agents as described herein may also be used to disrupt or enhance cell adhesion in a variety of other contexts. Within each of the methods described herein, one or more modulating agents may generally be administered alone, or within a pharmaceutical composition. In each specific method described herein, as noted above, a targeting agent may be employed to increase the local concentration of modulating agent at the target site.

Within one aspect, one or more modulating agents may be used for therapy of a demyelinating neurological disease in a mammal. There are a number of demyelinating diseases, such as multiple sclerosis, characterized by oligodendrocyte death. Since Schwann cell migration on astrocytes is inhibited by N-cadherin, modulating agents that disrupt N-cadherin mediated cell adhesion as described herein, when implanted with Schwann cells into the central nervous system, may facilitate Schwann cell migration and permit the practice of Schwann cell replacement therapy.

Multiple sclerosis patients suitable for treatment may be identified by criteria that establish a diagnosis of clinically definite or clinically probable MS (see Poser et al., *Ann. Neurol.* 13:227, 1983). Candidate patients for preventive therapy may be identified by the presence of genetic factors, such as HLA-type DR2a and DR2b, or by the presence of early disease of the relapsing remitting type. Schwann cell grafts may be implanted directly into the brain along with the modulating agent(s) using standard techniques. Suitable amounts of modulating agent generally range as described above, preferably from about 10 μg/mL to about 1 mg/mL.

Alternatively, a modulating agent may be implanted with oligodendrocyte progenitor cells (OPs) derived from donors not afflicted with the demyelinating disease. The myelinating cell of the CNS is the oligodendrocyte. Although mature oligodendrocytes and immature cells of the oligodendrocyte lineage, such as the oligodendrocyte type 2 astrocyte progenitor, have been used for transplantation, OPs are more widely used. OPs are highly motile and are able to migrate from transplant sites to lesioned areas where they differentiate into mature myelin-forming oligodendrocytes and contribute to repair of demyelinated axons (see e.g., Groves et al., *Nature* 362:453–55, 1993; Baron-Van Evercooren. et al., *Glia* 16:147–64, 1996). OPs can be isolated using routine techniques known in the art (see e.g., Milner and French-Constant, *Development* 120:3497–3506, 1994), from many regions of the CNS including brain, cerebellum, spinal cord, optic nerve and olfactory bulb. Substantially greater yields of OP's are obtained from embryonic or neonatal rather than adult tissue. OPs may be isolated from human embryonic spinal cord and cultures of neurospheres established. Human fetal tissue is a potential valuable and renewable source of donor OP's for future, long range transplantation therapies of demyelinating diseases such as MS.

OPs can be expanded in vitro if cultured as "homotypic aggregates" or "spheres" (Avellana-Adalid et al, *J. Neurosci. Res.* 45:558–70, 1996). Spheres (sometimes called "oligospheres" or "neurospheres") are formed when OPs are grown in suspension in the presence of growth factors such as PDGF and FGF. OPs can be harvested from spheres by mechanical dissociation and used for subsequent transplantation or establishment of new spheres in culture. Alternatively, the spheres themselves may be transplanted, providing a "focal reservoir" of OPs (Avellana-Adalid et al, *J. Neurosci. Res.* 45:558–70, 1996).

An alternative source of OP may be spheres derived from CNS stem cells. Recently, Reynolds and Weiss, *Dev. Biol.* 165:1–13, 1996 have described spheres formed from EGF-responsive cells derived from embryonic neuroepithelium, which appear to retain the pluripotentiality exhibited by neuroepithelium in vivo. Cells dissociated from these spheres are able to differentiate into neurons, oligodendrocytes and astrocytes when plated on adhesive substrates in the absence of EGF, suggesting that EGF-responsive cells derived from undifferentiated embryonic neuroepithelium may represent CNS stem cells (Reynolds and Weiss, *Dev. Biol.* 165:1–13, 1996). Spheres derived from CNS stem cells provide an alternative source of OP which may be manipulated in vitro for transplantation in vivo. Spheres composed of CNS stem cells may further provide a microenvironment conducive to increased survival, migration, and differentiation of the OPs in vivo.

The use of neurospheres for the treatment of MS may be facilitated by modulating agents that enhance cell migration from the spheres. In the absence of modulating agent, the cells within the spheres adhere tightly to one another and migration out of the spheres is hindered. Modulating agents that disrupt N-cadherin mediated cell adhesion as described herein, when injected with neurospheres into the central nervous system, may improve cell migration and increase the efficacy of OP replacement therapy. Neurosphere grafts may be implanted directly into the central nervous system along with the modulating agent(s) using standard techniques. Suitable amounts of modulating agent generally range as described above, preferably from about 10 µg/mL to about 1 mg/mL.

Alternatively, a modulating agent may be administered alone or within a pharmaceutical composition. The duration and frequency of administration will be determined by such factors as the condition of the patient, and the type and severity of the patient's disease. Within particularly preferred embodiments of the invention, the modulating agent or pharmaceutical composition may be administered at a dosage ranging from 0.1 mg/kg to 20 mg/kg although appropriate dosages may be determined by clinical trials. Methods of administration include injection, intravenous or intrathecal (i.e., directly in cerebrospinal fluid). A modulating agent or pharmaceutical composition may further comprise a drug (e.g., an immunomodulatory drug).

Effective treatment of multiple sclerosis may be evidenced by any of the following criteria: EDSS (extended disability status scale), appearance of exacerbations or MRI (magnetic resonance imaging). The EDSS is a means to grade clinical impairment due to MS (Kurtzke, *Neurology* 33:1444, 1983), and a decrease of one full step defines an effective treatment in the context of the present invention (Kurtzke, *Ann. Neurol.* 36:573–79, 1994). Exacerbations are defined as the appearance of a new symptom that is attributable to MS and accompanied by an appropriate new neurologic abnormality (Sipe et al., *Neurology* 34:1368, 1984). Therapy is deemed to be effective if there is a statistically significant difference in the rate or proportion of exacerbation-free patients between the treated group and the placebo group or a statistically significant difference in the time to first exacerbation or duration and severity in the treated group compared to control group. MRI can be used to measure active lesions using gadolinium-DTPA-enhanced imaging (McDonald et al. *Ann. Neurol.* 36:14, 1994) or the location and extent of lesions using $T_2$-weighted techniques. The presence, location and extent of MS lesions may be determined by radiologists using standard techniques. Improvement due to therapy is established when there is a statistically significant improvement in an individual patient compared to baseline or in a treated group versus a placebo group.

Efficacy of the modulating agent in the context of prevention may be judged based on clinical measurements such as the relapse rate and EDSS. Other criteria include a change in area and volume of T2 images on MRI, and the number and volume of lesions determined by gadolinium enhanced images.

Within other aspects, methods are provided in which cell adhesion is diminished. In one such aspect, the present invention provides methods for reducing unwanted cellular adhesion by administering a modulating agent as described herein. Unwanted cellular adhesion can occur between tumor cells, between tumor cells and normal cells or between normal cells as a result of surgery, injury, chemotherapy, disease, inflammation or other condition jeopardizing cell viability or function. Topical administration of the modulating agent(s) is generally preferred, but other means may also be employed. Preferably, a fluid composition for topical administration (comprising, for example, physiological saline) comprises an amount of modulating agent as described above, and more preferably from 10 µg/mL to 1 mg/mL. Creams may generally be formulated as described above. Topical administration in the surgical field may be given once at the end of surgery by irrigation of the wound or as an intermittent or continuous irrigation with the use of surgical drains in the post-operative period or by the use of drains specifically inserted in an area of inflammation, injury or disease in cases where surgery does not need to be performed. Alternatively, parenteral or transcutaneous administration may be used to achieve similar results.

Within another such aspect, methods are provided for enhancing the delivery of a drug through the skin of a mammal. Transdermal delivery of drugs is a convenient and non-invasive method that can be used to maintain relatively constant blood levels of a drug. In general, to facilitate drug delivery via the skin, it is necessary to perturb adhesion between the epithelial cells (keratinocytes) and the endothelial cells of the microvasculature. Using currently available techniques, only small, uncharged molecules may be delivered across skin in vivo. The methods described herein are not subject to the same degree of limitation. Accordingly, a wide variety of drugs may be transported across the epithelial and endothelial cell layers of skin, for systemic or topical administration. Such drugs may be delivered to melanomas or may enter the blood stream of the mammal for delivery to other sites within the body.

To enhance the delivery of a drug through the skin, a modulating agent as described herein and a drug are contacted with the skin surface. Contact may be achieved by direct application of the modulating agent, generally within a composition formulated as a cream or gel, or using any of a variety of skin contact devices for transdermal application (such as those described in European Patent Application No. 566,816 A; U.S. Pat. Nos. 5,613,958; 5,505,956). A skin patch provides a convenient method of administration (particularly for slow-release formulations). Such patches may contain a reservoir of modulating agent and drug separated from the skin by a membrane through which the drug diffuses. Within other patch designs, the modulating agent and drug may be dissolved or suspended in a polymer or adhesive matrix that is then placed in direct contact with the patient's skin. The modulating agent and drug may then diffuse from the matrix into the skin. Modulating agent(s) and drug(s) may be contained within the same composition or skin patch, or may be separately administered, although administration at the same time and site is preferred. In general, the amount of modulating agent administered via the skin varies with the nature of the condition to be treated or prevented, but may vary as described above. Such levels may be achieved by appropriate adjustments to the device used, or by applying a cream formulated as described above. Transfer of the drug across the skin and to the target tissue may be predicted based on in vitro studies using, for example, a Franz cell apparatus, and evaluated in vivo by appropriate means that will be apparent to those of ordinary skill in the art. As an example, monitoring of the serum level of the administered drug over time provides an easy measure of the drug transfer across the skin.

Transdermal drug delivery as described herein is particularly useful in situations in which a constant rate of drug delivery is desired, to avoid fluctuating blood levels of a drug. For example, morphine is an analgesic commonly used immediately following surgery. When given intermittently in a parenteral form (intramuscular, intravenous), the patient usually feels sleepy during the first hour, is well during the next 2 hours and is in pain during the last hour because the blood level goes up quickly after the injection and goes down below the desirable level before the 4 hour interval prescribed for re-injection is reached. Transdermal administration as described herein permits the maintenance of constant levels for long periods of time (e.g., days), which allows adequate pain control and mental alertness at the same time. Insulin provides another such example. Many diabetic patients need to maintain a constant baseline level of insulin which is different from their needs at the time of meals. The baseline level may be maintained using transdermal administration of insulin, as described herein. Antibiotics may also be administered at a constant rate, maintaining adequate bactericidal blood levels, while avoiding the high levels that are often responsible for the toxicity (e.g., levels of gentamycin that are too high typically result in renal toxicity).

Drug delivery by the methods of the present invention also provide a more convenient method of drug administration. For example, it is often particularly difficult to administer parenteral drugs to newborns and infants because of the difficulty associated with finding veins of acceptable caliber to catheterize. However, newborns and infants often have a relatively large skin surface as compared to adults. Transdermal drug delivery permits easier management of such patients and allows certain types of care that can presently be given only in hospitals to be given at home. Other patients who typically have similar difficulties with venous catheterization are patients undergoing chemotherapy or patients on dialysis. In addition, for patients undergoing prolonged therapy, transdermal administration as described herein is more convenient than parenteral administration.

Transdermal administration as described herein also allows the gastrointestinal tract to be bypassed in situations where parenteral uses would not be practical. For example, there is a growing need for methods suitable for administration of therapeutic small peptides and proteins, which are typically digested within the gastrointestinal tract. The methods described herein permit administration of such compounds and allow easy administration over long periods of time. Patients who have problems with absorption through their gastrointestinal tract because of prolonged ileus or specific gastrointestinal diseases limiting drug absorption may also benefit from drugs formulated for transdermal application as described herein.

Further, there are many clinical situations where it is difficult to maintain compliance. For example, patients with mental problems (e.g., patients with Alzheimer's disease or psychosis) are easier to manage if a constant delivery rate of drug is provided without having to rely on their ability to take their medication at specific times of the day. Also patients who simply forget to take their drugs as prescribed are less likely to do so if they merely have to put on a skin patch periodically (e.g., every 3 days). Patients with diseases that are without symptoms, like patients with hypertension, are especially at risk of forgetting to take their medication as prescribed.

For patients taking multiple drugs, devices for transdermal application such as skin patches may be formulated with combinations of drugs that are frequently used together. For example, many heart failure patients are given digoxin in combination with furosemide. The combination of both drugs into a single skin patch facilitates administration, reduces the risk of errors (taking the correct pills at the appropriate time is often confusing to older people), reduces the psychological strain of taking "so many pills," reduces skipped dosage because of irregular activities and improves compliance.

The methods described herein are particularly applicable to humans, but also have a variety of veterinary uses, such as the administration of growth factors or hormones (e.g., for fertility control) to an animal.

As noted above, a wide variety of drugs may be administered according to the methods provided herein. Some examples of drug categories that may be administered transdermally include anti-inflammatory drugs (e.g., in arthritis and in other condition) such as all NSAID, indomethacin, prednisone, etc.; analgesics (especially when oral absorption is not possible, such as after surgery, and when parenteral administration is not convenient or desirable), including morphine, codeine, Demerol, acetaminophen and combinations of these (e.g., codeine plus acetaminophen); antibiotics such as Vancomycin (which is not absorbed by the GI tract and is frequently given intravenously) or a combination of INH and Rifampicin (e.g., for tuberculosis); anticoagulants such as heparin (which is not well absorbed by the GI tract and is generally given parenterally, resulting in fluctuation in the blood levels with an increased risk of bleeding at high levels and risks of inefficacy at lower levels) and Warfarin (which is absorbed by the GI tract but cannot be administered immediately after abdominal surgery because of the normal ileus following the procedure); antidepressants (e.g., in situations where compliance is an issue as in Alzheimer's disease or when maintaining stable blood levels results in a significant reduction of anti-cholinergic side effects and better tolerance by patients), such as amitriptylin, imipramin, prozac, etc.; antihypertensive drugs (e.g., to improve compliance and reduce side effects associated with fluctuating blood levels), such as diuretics and beta-blockers (which can be administered by the same patch; e.g., furosemide and propanolol); antipsychotics (e.g., to facilitate compliance and make it easier for care giver and family members to make sure that the drug is received), such as haloperidol and chlorpromazine; and anxiolytics or sedatives (e.g., to avoid the reduction of alertness related to high blood levels after oral administration and allow a continual benefit throughout the day by maintaining therapeutic levels constant).

Numerous other drugs may be administered as described herein, including naturally occurring and synthetic hormones, growth factors, proteins and peptides. For example, insulin and human growth hormone, growth factors like erythropoietin, interleukins and inteferons may be delivered via the skin.

Kits for administering a drug via the skin of a mammal are also provided within the present invention. Such kits generally comprise a device for transdermal application (e.g., a skin patch) in combination with, or impregnated with, one or more modulating agents. A drug may additionally be included within such kits.

Within a related aspect, the use of modulating agents as described herein to increase skin permeability may also facilitate sampling of the blood compartment by passive diffusion, permitting detection and/or measurement of the levels of specific molecules circulating in the blood. For example, application of one or more modulating agents to the skin, via a skin patch as described herein, permits the patch to function like a sponge to accumulate a small quantity of fluid containing a representative sample of the serum. The patch is then removed after a specified amount of time and analyzed by suitable techniques for the compound of interest (e.g., a medication, hormone, growth factor, metabolite or marker). Alternatively, a patch may be impregnated with reagents to permit a color change if a specific substance (e.g., an enzyme) is detected. Substances that can be detected in this manner include, but are not limited to, illegal drugs such as cocaine, HIV enzymes, glucose and PSA. This technology is of particular benefit for home testing kits.

Within a further aspect, methods are provided for enhancing delivery of a drug to a tumor in a mammal, comprising administering a modulating agent in combination with a drug to a tumor-bearing mammal. Preferably, the modulating agent and the drug are formulated within the same composition or drug delivery device prior to administration. In general, a modulating agent may enhance drug delivery to any tumor, and the method of administration may be chosen based on the type of target tumor. For example, injection or topical administration as described above may be preferred for melanomas and other accessible tumors (e.g., metastases from primary ovarian tumors may be treated by flushing the peritoneal cavity with the composition). Other tumors (e.g., bladder tumors) may be treated by injection of the modulating agent and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., mitomycin C for bladder cancer). In general, the amount of modulating agent administered varies with the method of administration and the nature of the tumor, within the typical ranges provided above, preferably ranging from about 1 $\mu$g/mL to about 2 mg/mL, and more preferably from about 10 $\mu$g/mL to 1 mg/mL. Transfer of the drug to the target tumor may be evaluated by appropriate means that will be apparent to those of ordinary skill in the art. Drugs may also be labeled (e.g., using radionuclides) to permit direct observation of transfer to the target tumor using standard imaging techniques.

Within a related aspect, the present invention provides methods for treating cancer and/or inhibiting metastasis in a mammal. Cancer tumors are solid masses of cells, growing out of control, which require nourishment via blood vessels. The formation of new capillaries is a prerequisite for tumor growth and the emergence of metastases. Administration of modulating agents as described herein may disrupt the growth of such blood vessels, thereby providing effective therapy for the cancer and/or inhibiting metastasis. Modulating agents may also be used to treat leukemias.

A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. In general, the amount of modulating agent administered varies depending upon the method of administration and the nature of the cancer, but may vary within the ranges identified above. The effectiveness of the cancer treatment or inhibition of metastasis may be evaluated using well known clinical observations, such as the level of serum tumor markers (e.g., CEA or PSA).

Within a further related aspect, a modulating agent may be used to inhibit angiogenesis (i.e., the growth of blood vessels from pre-existing blood vessels) in a mammal. Inhibition of angiogenesis may be beneficial, for example, in patients afflicted with diseases such as cancer or arthritis.

The effect of a particular modulating agent on angiogenesis may generally be determined by evaluating the effect of the agent on blood vessel formation. Such a determination may generally be performed, for example, using a chick chorioallantoic membrane assay (Iruela-Arispe et al., *Molecular Biology of the Cell* 6:327–343, 1995). Briefly, a modulating agent may be embedded in a mesh composed of vitrogen at one or more concentrations (e.g., ranging from about 1 to 100 $\mu$g/mesh). The mesh(es) may then be applied to chick chorioallantoic membranes. After 24 hours, the effect of the modulating agent may be determined using computer assisted morphometric analysis. A modulating agent should inhibit angiogenesis by at least 25% at a concentration of 33 $\mu$g/mesh.

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

In yet another related aspect, the present invention provides methods for inducing apoptosis in a cadherin-expressing cell. In general, patients afflicted with cancer may benefit from such treatment. Administration may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

The present invention also provides methods for enhancing drug delivery to the central nervous system of a mammal. The blood/brain barrier is largely impermeable to most neuroactive agents, and delivery of drugs to the brain of a mammal often requires invasive procedures. Using a modulating agent as described herein, however, delivery may be by, for example, systemic administration of a modulating agent-drug-targeting agent combination, injection of a modulating agent (alone or in combination with a drug and/or targeting agent) into the carotid artery or application of a skin patch comprising a modulating agent to the head of the patient.

In general, the amount of modulating agent administered varies with the method of administration and the nature of the condition to be treated or prevented, but typically varies as described above. Transfer of the drug to the central nervous system may be evaluated by appropriate means that will be apparent to those of ordinary skill in the art, such as magnetic resonance imaging (MRI) or PET scan (positron emitted tomography).

Within further aspects, modulating agents as described herein may be used for modulating the immune system of a mammal in any of several ways. Cadherins are expressed on immature B and T cells (thymocytes and bone marrow pre-B cells), as well as on specific subsets of activated B and T lymphocytes and some hematological malignancies (see Lee et al., *J. Immunol.* 152:5653–5659, 1994; Munro et al., *Cellular Immunol.* 169:309–312, 1996; Tsutsui et al., *J.*

*Biochem.* 120:1034–1039, 1996; Cepek et al., *Proc. Natl. Acad. Sci. USA* 93:6567–6571, 1996). Modulating agents may generally be used to modulate specific steps within cellular interactions during an immune response or during the dissemination of malignant lymphocytes.

For example, a modulating agent as described herein may be used to treat diseases associated with excessive generation of otherwise normal T cells. Without wishing to be bound by any particular, theory, it is believed that the interaction of cadherins on maturing T cells and B cell subsets contributes to protection of these cells from programmed cell death. A modulating agent may decrease such interactions, leading to the induction of programmed cell death. Accordingly, modulating agents may be used to treat certain types of diabetes and rheumatoid arthritis, particularly in young children where the cadherin expression on thymic pre-Tcells is greatest.

Modulating agents may also be administered to patients afflicted with certain skin disorders (such as cutaneous lymphomas), acute B cell leukemia and excessive immune reactions involving the humoral immune system and generation of immunoglobulins, such as allergic responses and antibody-mediated graft rejection. In addition, patients with circulating cadherin-positive malignant cells (e.g., during regimes where chemotherapy or radiation therapy is eliminating a major portion of the malignant cells in bone marrow and other lymphoid tissue) may benefit from treatment with a modulating agent. Such treatment may also benefit patients undergoing transplantation with peripheral blood stem cells.

Within the above methods, the modulating agent(s) are preferably administered systemically (usually by injection) or topically. A modulating agent may be linked to a targeting agent. For example, targeting to the bone marrow may be beneficial. A suitable dosage is sufficient to effect a statistically significant reduction in the population of B and/or T cells that express cadherin and/or an improvement in the clinical manifestation of the disease being treated. Typical dosages generally range as described above.

Within further aspects, the present invention provides methods and kits for preventing pregnancy in a mammal. In general, disruption of E-cadherin function prevents the adhesion of trophoblasts and their subsequent fusion to form syncitiotrophoblasts. In one embodiment, one or more modulating agents as described herein may be incorporated into any of a variety of well known contraceptive devices, such as sponges suitable for intravaginal insertion (see, e.g., U.S. Pat. No. 5,417,224) or capsules for subdermal implantation. Other modes of administration are possible, however, including transdermal administration, for modulating agents linked to an appropriate targeting agent.

Suitable methods for incorporation into a contraceptive device depend upon the type of device and are well known in the art. Such devices facilitate administration of the modulating agent(s) to the uterine region and may provide a sustained release of the modulating agent(s). In general, modulating agent(s) may be administered via such a contraceptive device at a dosage ranging from 0.1 to 50 mg/kg, although appropriate dosages may be determined by monitoring hCG levels in the urine. hCG is produced by the placenta, and levels of this hormone rise in the urine of pregnant women. The urine hCG levels can be assessed by radio-immunoassay using well known techniques. Kits for preventing pregnancy generally comprise a contraceptive device impregnated with one or more modulating agents.

Alternatively, a sustained release formulation of one or more modulating agents may be implanted, typically subdermally, in a mammal for the prevention of pregnancy.

Such implantation may be performed using well known techniques. Preferably, the implanted formulation provides a dosage as described above, although the minimum effective dosage may be determined by those of ordinary skill in the art using, for example, an evaluation of hCG levels in the urine of women.

The present invention also provides methods for increasing vasopermeability in a mammal by administering one or more modulating agents or pharmaceutical compositions. Within blood vessels, endothelial cell adhesion (mediated by N-cadherin) results in decreased vascular permeability. Accordingly, modulating agents as described herein that decrease N-cadherin mediated adhesion may be used to increase vascular permeability.

Within certain embodiments, preferred modulating agents for use within such methods include peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers.

Treatment with a modulating agent may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Within a further aspect, modulating agents as described herein may be used for controlled inhibition of synaptic stability, resulting in increased synaptic plasticity. Within this aspect, administration of one or more modulating agents may be advantageous for repair processes within the brain, as well as learning and memory, in which neural plasticity is a key early event in the remodeling of synapses. Cell adhesion molecules, particularly N-cadherin and E-cadherin, can function to stabilize synapses, and loss of this function is thought to be the initial step in the remodeling of the synapse that is associated with learning and memory (Doherty et al.,*J. Neurobiology,* 26:437–446, 1995; Martin and Kandel, *Neuron,* 17:567–570, 1996; Fannon and Colman, *Neuron,* 17:423–434, 1996). Inhibition of cadherin function by administration of one or more modulating agents may stimulate learning and memory. For such aspects, administration may be via encapsulation into a delivery vehicle such as a liposome, using standard techniques, and injection into, for example, the carotid artery. Alternatively, a modulating agent may be linked to a disrupter of the blood-brain barrier. In general dosages range as described above.

The following examples are offered by way of illustration and not by way of limitation.

EXAMPLES

Example 1

Preparation of Representative Modulating Agents

This Example illustrates the solid phase synthesis of representative peptide modulating agents.

The peptides were synthesized on a 431A Applied Biosystems peptide synthesizer using p-Hydroxymethylphenoxymethyl polystyrene (HMP) resin and standard Fmoc chemistry. After synthesis and deprotection, the peptides were de-salted on a Sephadex G-10 column and lyophilized. The peptides were analyzed for purity by analytical HPLC, and in each case a single peak was observed. Peptides were made as stock solutions at 10 to 25 mg/mL in dimethylsulfoxide (DMSO) or water and stored at −20° C. before use.

Representative peptides synthesized by this method are illustrated below:

Example 2

Disruption of Interactions between α-catenin and β-catenin

This Example illustrates the use of representative modulating agents to disrupt interactions between α-catenin and β-catenin.

The linear peptide H-CKHAVVNC-OH (SEQ ID NO:4; Example 1, upper structure) and the cyclic peptide H-CKHAVVNC-OH (SEQ ID NO:5; Example 1, lower structure) were synthesized using standard solid phase peptide synthesis techniques as described above. Both of these peptides contain the amino acid sequence HAV. In addition, the cyclic peptide has a disulfide tether, Ac-Cys-S-S-Cys-NH$_2$.

Figure 5:
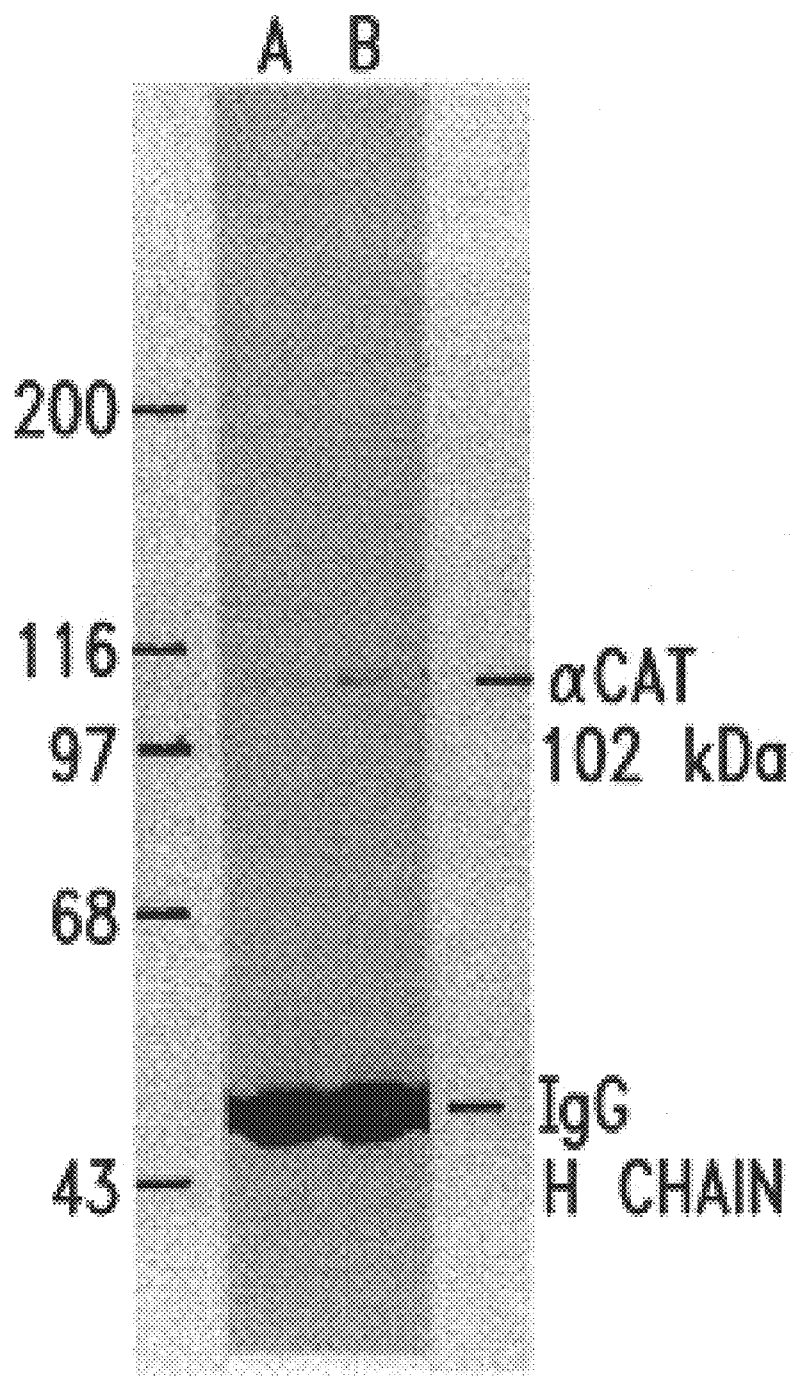
FIG. 5 is a Western blot of proteins immunoprecipitated from adult mouse brain extracts utilizing anti-β-catenin antibodies in the presence of either the representative modulating agent H-CKHAVVNC-OH (SEQ ID NO:4; Lane A) or the control peptide H-CKHGVVNC-OH (SEQ ID NO:6; Lane B) and probed with anti-β-catenin antibodies.

These peptides, as well as two control peptides (H-CKHGVVNC-OH, SEQ ID NO:6, and H-CKHGVVNC-OH, SEQ ID NO:51) were analyzed for their ability to disrupt α-catenin/β-catenin interactions, as judged by standard immunoprecipitation methods. FIG. 5 shows a Western blot of proteins immunoprecipitated from mouse brain extracts in the presence of either H-CKHAVVNC-OH (SEQ ID NO:4; lane A) or H-CKHGVVNC-OH (SEQ ID NO:6; lane B) and probed with anti-α-catenin antibodies. Brains from adult mice were homogenized in TC buffer (10

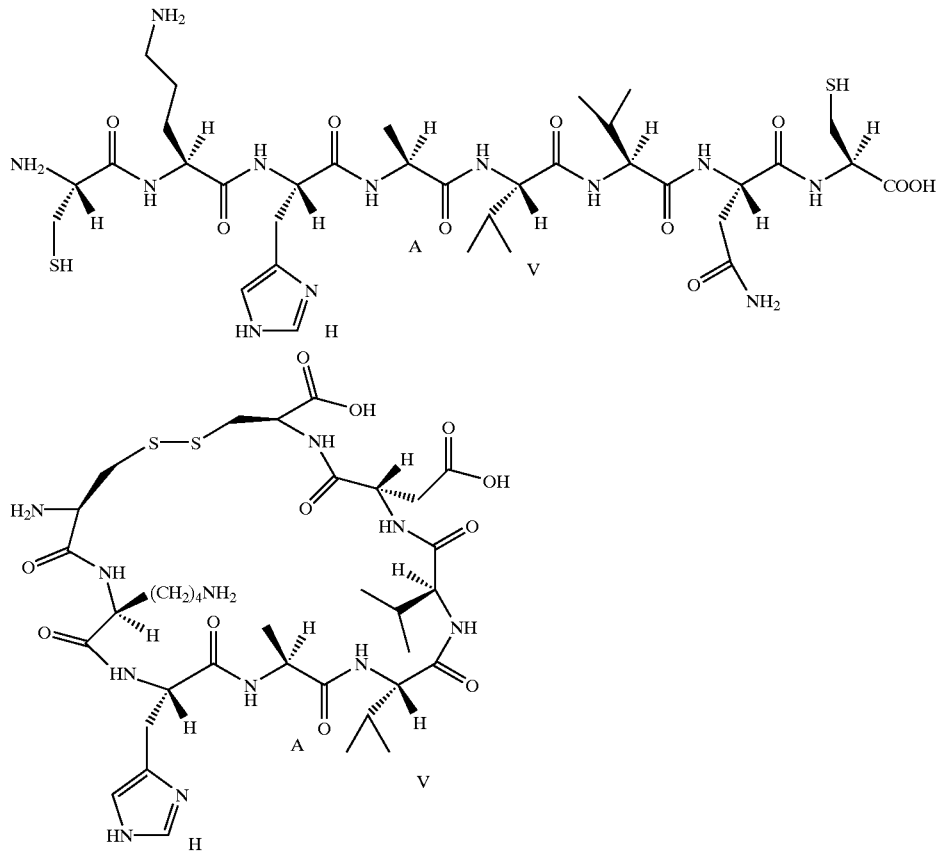

mM Tris pH 6.8 containing 1 mM $CaCl_2$, 500 μM phenylmethylsulfonylfluoride, 10 μg/ml leupeptin, 10 μg/ml aprotinin, and 5 μg/ml pepstatin) at wet weight to volume ratio of 1:2. Five-fold concentrated IP buffer (50 mM Tris pH 7.4 containing 750 mM NaCl, 5% Triton X-100, 2.5% NP-40) was then added to the homogenate at a volume to volume ratio of 1:4. The homogenate was then incubated with continuous agitation for 3 hours at 4° C. in the presence of either H-CKHAVVNC-OH (SEQ ID NO:4) or H-CKHGVVNC-OH (SEQ ID NO:6) at a concentration of 1 mg/ml. At the end of the incubation period, the homogenate was centrifuged (10,000×g) for 5 minutes at 4° C. Aliquots (50 μl) of the supernatant were incubated with 1.25 μg mouse monoclonal anti-β-catenin antibody (Transduction Laboratories, Lexington, Ky.) with continuous agitation for 18 hours at 4° C. An aliquot (25 μl) of Protein G Sepharose (Pharmacia Biotech, Baie d'Urfe, Quebec) suspended in one-fold concentrated IP buffer containing 500 μM phenylmethylsulfonylfluoride, 10 μg/ml leupeptin, 10 μg/ml aprotinin, and 5 μg/ml pepstatin was added to each incubation mixture and the mixtures were incubated with continuous agitation for an additional 4 hours at 4° C. The mixtures were then centrifuged (5,000×g) for 5 minutes at 4° C. Immunoprecipitates were washed five times with one-fold concentrated IP buffer and resuspended in solubilization buffer (62.5 mM Tris pH6.8 containing 2% SDS, 10% glycerol, and 5% β-mercaptoethanol). The suspensions were heated at 100° C. for 5 minutes, and then subjected to SDS-PAGE. Following PAGE, the proteins were electrophoretically transferred to nitrocellulose membrane (0.22 μm pore size; Micron Separations Inc., Westboro, Mass.). The membrane was incubated for 1 hour in TTBS buffer (25 mM Tris pH 7.6, 0.1% Tween 20 and 0.9% w/v NaCl) containing 5% w/v dry skimmed milk, and then incubated for 1 hour in TTBS containing mouse anti-α-catenin antibodies (diluted 1:500; Transduction Laboratories, Lexington, Ky.). The membrane was washed 3 times with TTBS, and incubated for 45 minutes in TTBS containing goat anti-mouse IgG antibody conjugated to horseradish peroxidase (diluted 1:5000; Kirkegaard and Perry Laboratories, Gaithersburg, Md.). Finally, the membrane was washed 3 times with TTBS, and the immunoreactive proteins were detected using an enhanced chemiluminescence kit (ECL; Amersham Life Sciences Inc., Oakville, Ontario) and autoradiographic film (Fuji, Minami-Ashigara, Japan). Molecular mass markers (in kDa) are shown on the left-hand side of the blot. α-catenin (αCAT; molecular mass 102 kDa) is indicated on the right-hand side of the blot. Mouse immunoglobulin G was also immunoprecipitated. The mouse immunoglobulin G heavy chain (IgG H CHAIN) is indicated on the right-hand side of the blot.

The Western blot shown in FIG. 5 was stripped and re-probed with anti-β-catenin antibodies (diluted 1:500 in TTBS; Transduction Laboratories, Lexington, Ky.). FIG. 6 shows the Western blot which was probed with the β-catenin antibodies. Molecular mass markers (in kDa) are shown on the left-hand side of the blot. β-catenin (βCAT; molecular mass 95 kDa) is indicated on the right-hand side of the blot. Mouse immunoglobulin G was also immunoprecipitated. The mouse immunoglobulin G heavy chain (IgG H CHAIN) is indicated on the right-hand side of the blot.

Only the results obtained utilizing the linear peptides H-CKHAVVNC-OH(SEQ ID NO:4) and H-CKHGVVNC-OH (SEQ ID NO:6) are shown, as similar results were obtained using the cyclic peptides H-CKHAVVNC-OH (SEQ ID NO:5) and H-CKHGVVNC-OH (SEQ ID NO:51). In the presence of either linear or cyclic peptides containing the β-catenin HAV motif, α-catenin was immunoprecipitated to a lesser extent from the adult mouse brain extracts than in the presence of the control peptides. Therefore, both linear and cyclic peptides containing the HAV motif (amino acid sequences H-CKHAVVNC-OH (SEQ ID NO:4) and H-CKHAVVNC-OH (SEQ ID NO:5), respectively; FIG. 2) are capable of disrupting the interaction between α-catenin and β-catenin. None of the peptides affected the ability of the anti-β-catenin antibodies to immunoprecipitate β-catenin (molecular mass 95 kDa; FIG. 6).

Example 3

Disruption of Cell Adhesion

This Example illustrates the use of representative modulating agents to inhibit cadherin-mediated cell adhesion.

Three peptides (N-Ac-CKHAVVNC-$NH_2$, N-Ac-CKHGVVNC-$NH_2$, and H-KHAVVN-OH; SEQ ID NOS: 5, 51 and 8 respectively) were tested for their ability to disrupt cell adhesion. Normal human breast A1N4 cells were grown on gridded glass coverslips to approximately 30% confluence. Peptides were dissolved in distilled water at a concentration of 100 μg/ml. Each of the three peptide solutions was mixed 1:1 with a solution containing the fluorescent marker DAPI (Molecular Probes Inc., Eugene, Oreg.) dissolved in water at a concentration of 40 μg/ml. All of the mixtures were centrifuged at 10,000×g for 5 minutes immediately before use in the experiments. An aliquot (3 ml) of each peptide/DAPI mixture was taken up in an Eppendorff microinjection pipette. Microinjection was performed using an Eppendorf microinjector and micromanipulator coupled to an IM35 inverted Zeiss microscope with phase contrast and Hoffman optics. Cells to be injected were located and their position on the grid noted. For microinjection, the pipette was brought close to the cell layer and the micromanipulator programmed to return to the same plane. Cells were injected with 0.2 pL of peptide/DAPI mixture. This corresponds to approximately 1/100 of the cell volume and results in a final intracellular concentration of peptide of 0.5 mg/ml. The morphology of the injected cells was noted at hourly intervals. After 4 hours, a difference in the morphology of the cells injected with the various peptides was observed. Cells injected with the peptides N-Ac-CKHAVVNC-$NH_2$ (SEQ ID NO:5) and N-Ac-CKHGVVNC-$NH_2$ (SEQ ID NO:51) were indistinguishable from surrounding uninjected cells. In contrast, cells injected with the peptide H-KHAVVN-OH (SEQ ID NO:8) had become rounded, and they were detached from their neighbors. This result suggests that the peptide H-KHAVVN-OH (SEQ ID NO:8) is capable of disrupting the interaction between α-catenin and β-catenin, thus causing a disruption of cadherin-mediated cell adhesion. These results also indicate that protection of the C-terminus and N-terminus of a peptide renders the peptide inactive (compare the results for N-Ac-CKHAVVNC-NH, (SEQ ID NO:5) in this Example with H-CKHAVVNC-OH (SEQ ID NO:5) in Example 2).

From the foregoing, it will be evident that although specific embodiments of the invention have been described herein for the purpose of illustrating the invention, various modifications may be made without deviating from the spirit and scope of the invention.

What is claimed is:

1. A modulating agent for inhibiting an interaction between α-catenin and β-catenin, comprising
the amino acid sequence KHAVV (SEQ ID NO:1).

2. A modulating agent according to claim 1, wherein the modulating agent comprises the linear peptide sequence KHAVV (SEQ ID NO:1).

3. A modulating agent according to claim 2, wherein the modulating agent comprises a sequence selected from the group consisting of KHAVVN (SEQ ID NO:8), LKHAVVN (SEQ ID NO:9), LKHAVV (SEQ ID NO:10), CKHAVVNC (SEQ ID NO:4), CLKHAVVNC (SEQ ID NO:12), CLKHAVVC (SEQ ID NO:13) and CKHAVVC (SEQ ID NO:15).

4. A modulating agent according to claim 1, wherein the modulating agent comprises a cyclic peptide ring comprising the sequence KHAVV (SEQ ID NO:1).

5. A modulating agent according to claim 4, wherein the cyclic peptide sequence is selected from the group consisting of CKHAVVNC (SEQ ID NO:5), CLKHAVVNC (SEQ ID NO:23), CLKHAVVC (SEQ ID NO:24), CKHAVVC (SEQ ID NO:25), KHAVVND (SEQ ID NO:26), KHAVVNE (SEQ ID NO:27), KHAVVD (SEQ ID NO:28) and KHAVVE (SEQ ID NO:29).

6. A modulating agent according to claim 1, wherein the modulating agent comprises a linear or cyclic peptide ranging from 5 to 16 amino acid residues in length.

7. A modulating agent for inhibiting an interaction between α-catenin and β-catenin, comprising
a β-catenin HAV motif
wherein the modulating agent is associated with an internalization moiety.

8. A modulating agent according to claim 7, wherein the modulating agent comprises a linear peptide sequence.

9. A modulating agent according to claim 8, wherein the peptide sequence is selected from the group consisting of KHAVVN (SEQ ID NO:8), LKHAVVN (SEQ ID NO:9), LKHAVV (SEQ ID NO:10), LKHAV (SEQ ID NO:11), KHAVV (SEQ ID NO:1), CKHAVVNC (SEQ ID NO:4), CLKHAVVNC (SEQ ID NO:12), CLKHAVVC (SEQ ID NO:13), CLKHAVC (SEQ ID NO:14), CKHAVVC (SEQ ID NO:15), KHAV (SEQ ID NO:16), HAVVN (SEQ ID NO:17), HAVN (SEQ ID NO:18), HAV, CKHAVC (SEQ ID NO:19), CHAVVNC (SEQ ID NO:20), CHAVVC (SEQ ID NO:21) and CHAVC (SEQ ID NO:22).

10. A modulating agent according to claim 7, wherein the modulating agent comprises a cyclic peptide sequence.

11. A modulating agent according to claim 10, wherein the cyclic peptide sequence is selected from the group consisting of CKHAVVNC (SEQ ID NO:5), CLKHAVVNC (SEQ ID NO:23), CLKHAVVC (SEQ ID NO:24), CKHAVVC (SEQ ID NO:25), KHAVVND (SEQ ID NO:26), KHAVVNE (SEQ ID NO:27), KHAVVD (SEQ ID NO:28), KHAVVE (SEQ ID NO:29), CLKHAVC (SEQ ID NO:30), CKHAVC (SEQ ID NO:31), CHAVVNC (SEQ ID NO:32), CHAVVC (SEQ ID NO:33), CHAVC (SEQ ID NO:34), KHAVD (SEQ ID NO:35) and KHAVE (SEQ ID NO:36).

12. A modulating agent according to claim 7, wherein the modulating agent comprises a linear or cyclic peptide ranging from 3 to 16 amino acid residues in length.

13. A modulating agent according to claim 7, wherein the internalization moiety is an internalization sequence covalently linked to the modulating agent.

14. A modulating agent according to claim 13, wherein the internalization sequence comprises a sequence selected from the group consisting of RQIKIWFQNRRMKWKK (SEQ ID NO:47), RQIKIWPQNRRNKWKK (SEQ ID NO:48) and KKWKKWWKKWWKKWKK (SEQ ID NO:49).

15. A modulating agent according to claim 7, wherein the internalization moiety is a liposome, and wherein the modulating agent is encapsulated within the liposome.

16. A modulating agent according to claim 1 or claim 7, wherein the modulating agent is linked to a targeting agent.

17. A modulating agent according to claim 1 or claim 7, wherein the modulating agent is linked to a drug.

18. A composition comprising a modulating agent according to claim 1 or claim 7, in combination with a pharmaceutically acceptable carrier.

19. A composition according to claim 18, further comprising a drug.

20. A composition according to claim 18, wherein the cell adhesion modulating agent is present within a sustained-release formulation.

21. A kit for enhancing transdermal drug delivery, comprising:
(a) a skin patch; and
(b) a modulating agent according to claim 1 or claim 7.

22. A kit according to claim 21, wherein the skin patch is impregnated with the modulating agent.

23. A kit according to claim 21, further comprising a drug.

* * * * *

SEQUENCE LISTING (1) GENERAL INFORMATION:

(iii) NUMBER OF SEQUENCES: 73

(2) INFORMATION FOR SEQ ID NO: 1:

(i) SEQUENCE CHARACTERISTICS:
      (A) LENGTH: 5 amino acids
      (B) TYPE: amino acid
      (C) STRANDEDNESS: <Unknown>
      (D) TOPOLOGY: both (xi) SEQUENCE DESCRIPTION: SEQ ID NO: 1:

Lys His Ala Val Val
1          5

(2) INFORMATION FOR SEQ ID NO: 2:

(i) SEQUENCE CHARACTERISTICS:
      (A) LENGTH: 5 amino acids
      (B) TYPE: amino acid
      (C) STRANDEDNESS: <Unknown>
      (D) TOPOLOGY: linear (xi) SEQUENCE DESCRIPTION: SEQ ID NO: 2:

Asp Xaa Asn Asp Asn
1          5

(2) INFORMATION FOR SEQ ID NO: 3:

(i) SEQUENCE CHARACTERISTICS:
      (A) LENGTH: 4 amino acids
      (B) TYPE: amino acid
      (C) STRANDEDNESS: <Unknown>
      (D) TOPOLOGY: linear (xi) SEQUENCE DESCRIPTION: SEQ ID NO: 3:

Leu Asp Arg Glu
1

(2) INFORMATION FOR SEQ ID NO: 4:

(i) SEQUENCE CHARACTERISTICS:
      (A) LENGTH: 8 amino acids
      (B) TYPE: amino acid
      (C) STRANDEDNESS: <Unknown>
      (D) TOPOLOGY: linear (xi) SEQUENCE DESCRIPTION: SEQ ID NO: 4:

Cys Lys His Ala Val Val Asn Cys
1          5

(2) INFORMATION FOR SEQ ID NO: 5:

(i) SEQUENCE CHARACTERISTICS:
      (A) LENGTH: 8 amino acids
      (B) TYPE: amino acid
      (C) STRANDEDNESS: <Unknown>
      (D) TOPOLOGY: circular (xi) SEQUENCE DESCRIPTION: SEQ ID NO: 5:

Cys Lys His Ala Val Val Asn Cys
1          5

(2) INFORMATION FOR SEQ ID NO: 6:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: linear (xi) SEQUENCE DESCRIPTION: SEQ ID NO: 6:

Cys Lys His Gly Val Val Asn Cys
1               5

(2) INFORMATION FOR SEQ ID NO: 7:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (xi) SEQUENCE DESCRIPTION: SEQ ID NO: 7:

Leu Lys His Ala Val Val Asn Leu Ile Asn
1               5                   10

(2) INFORMATION FOR SEQ ID NO: 8:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (xi) SEQUENCE DESCRIPTION: SEQ ID NO: 8:

Lys His Ala Val Val Asn
1               5

(2) INFORMATION FOR SEQ ID NO: 9:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (xi) SEQUENCE DESCRIPTION: SEQ ID NO: 9:

Leu Lys His Ala Val Val Asn
1               5

(2) INFORMATION FOR SEQ ID NO: 10:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (xi) SEQUENCE DESCRIPTION: SEQ ID NO: 10:

Leu Lys His Ala Val Val
1               5

(2) INFORMATION FOR SEQ ID NO: 11:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (xi) SEQUENCE DESCRIPTION: SEQ ID NO: 11:

```
Leu Lys His Ala Val
 1               5

(2) INFORMATION FOR SEQ ID NO: 12:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (xi) SEQUENCE DESCRIPTION: SEQ ID NO: 12:

Cys Leu Lys His Ala Val Val Asn Cys
 1               5

(2) INFORMATION FOR SEQ ID NO: 13:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (xi) SEQUENCE DESCRIPTION: SEQ ID NO: 13:

Cys Leu Lys His Ala Val Val Cys
 1               5

(2) INFORMATION FOR SEQ ID NO: 14:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (xi) SEQUENCE DESCRIPTION: SEQ ID NO: 14:

Cys Leu Lys His Ala Val Cys
 1               5

(2) INFORMATION FOR SEQ ID NO: 15:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (xi) SEQUENCE DESCRIPTION: SEQ ID NO: 15:

Cys Lys His Ala Val Val Cys
 1               5

(2) INFORMATION FOR SEQ ID NO: 16:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (xi) SEQUENCE DESCRIPTION: SEQ ID NO: 16:

Lys His Ala Val
 1

(2) INFORMATION FOR SEQ ID NO: 17:

(i) SEQUENCE CHARACTERISTICS:
        (A) LENGTH: 5 amino acids
        (B) TYPE: amino acid
```

(C) STRANDEDNESS: <Unknown>
            (D) TOPOLOGY: linear (xi) SEQUENCE DESCRIPTION: SEQ ID NO: 17:

His Ala Val Val Asn
1               5

(2) INFORMATION FOR SEQ ID NO: 18:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (xi) SEQUENCE DESCRIPTION: SEQ ID NO: 18:

His Ala Val Asn
1

(2) INFORMATION FOR SEQ ID NO: 19:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (xi) SEQUENCE DESCRIPTION: SEQ ID NO: 19:

Cys Lys His Ala Val Cys
1               5

(2) INFORMATION FOR SEQ ID NO: 20:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (xi) SEQUENCE DESCRIPTION: SEQ ID NO: 20:

Cys His Ala Val Val Asn Cys
1               5

(2) INFORMATION FOR SEQ ID NO: 21:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (xi) SEQUENCE DESCRIPTION: SEQ ID NO: 21:

Cys His Ala Val Val Cys
1               5

(2) INFORMATION FOR SEQ ID NO: 22:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (xi) SEQUENCE DESCRIPTION: SEQ ID NO: 22:

Cys His Ala Val Cys
1               5

(2) INFORMATION FOR SEQ ID NO: 23:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: circular (xi) SEQUENCE DESCRIPTION: SEQ ID NO: 23:

Cys Leu Lys His Ala Val Val Asn Cys
1           5

(2) INFORMATION FOR SEQ ID NO: 24:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: circular (xi) SEQUENCE DESCRIPTION: SEQ ID NO: 24:

Cys Leu Lys His Ala Val Val Cys
1           5

(2) INFORMATION FOR SEQ ID NO: 25:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: circular (xi) SEQUENCE DESCRIPTION: SEQ ID NO: 25:

Cys Lys His Ala Val Val Cys
1           5

(2) INFORMATION FOR SEQ ID NO: 26:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: circular (xi) SEQUENCE DESCRIPTION: SEQ ID NO: 26:

Lys His Ala Val Val Asn Asp
1           5

(2) INFORMATION FOR SEQ ID NO: 27:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: circular (xi) SEQUENCE DESCRIPTION: SEQ ID NO: 27:

Lys His Ala Val Val Asn Glu
1           5

(2) INFORMATION FOR SEQ ID NO: 28:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: circular (xi) SEQUENCE DESCRIPTION: SEQ ID NO: 28:

```
Lys His Ala Val Val Asp
1               5
```

(2) INFORMATION FOR SEQ ID NO: 29:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: circular (xi) SEQUENCE DESCRIPTION: SEQ ID NO: 29:

```
Lys His Ala Val Val Glu
1               5
```

(2) INFORMATION FOR SEQ ID NO: 30:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: circular (xi) SEQUENCE DESCRIPTION: SEQ ID NO: 30:

```
Cys Leu Lys His Ala Val Cys
1               5
```

(2) INFORMATION FOR SEQ ID NO: 31:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: circular (xi) SEQUENCE DESCRIPTION: SEQ ID NO: 31:

```
Cys Lys His Ala Val Cys
1               5
```

(2) INFORMATION FOR SEQ ID NO: 32:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: circular (xi) SEQUENCE DESCRIPTION: SEQ ID NO: 32:

```
Cys His Ala Val Val Asn Cys
1               5
```

(2) INFORMATION FOR SEQ ID NO: 33:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: circular (xi) SEQUENCE DESCRIPTION: SEQ ID NO: 33:

```
Cys His Ala Val Val Cys
1               5
```

(2) INFORMATION FOR SEQ ID NO: 34:

(i) SEQUENCE CHARACTERISTICS:
        (A) LENGTH: 5 amino acids (B) TYPE: amino acid
        (C) STRANDEDNESS: <Unknown>
        (D) TOPOLOGY: circular (xi) SEQUENCE DESCRIPTION: SEQ ID NO: 34:

Cys His Ala Val Cys
1               5

(2) INFORMATION FOR SEQ ID NO: 35:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: circular (xi) SEQUENCE DESCRIPTION: SEQ ID NO: 35:

Lys His Ala Val Asp
1               5

(2) INFORMATION FOR SEQ ID NO: 36:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: circular (xi) SEQUENCE DESCRIPTION: SEQ ID NO: 36:

Lys His Ala Val Glu
1               5

(2) INFORMATION FOR SEQ ID NO: 37:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: circular (xi) SEQUENCE DESCRIPTION: SEQ ID NO: 37:

Lys His Ala Val Val Asn
1               5

(2) INFORMATION FOR SEQ ID NO: 38:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: circular (xi) SEQUENCE DESCRIPTION: SEQ ID NO: 38:

Leu Lys His Ala Val Val Asn
1               5

(2) INFORMATION FOR SEQ ID NO: 39:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: circular (xi) SEQUENCE DESCRIPTION: SEQ ID NO: 39:

His Ala Val Val Asn
1               5

(2) INFORMATION FOR SEQ ID NO: 40:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: circular (xi) SEQUENCE DESCRIPTION: SEQ ID NO: 40:

His Ala Val Val
1

(2) INFORMATION FOR SEQ ID NO: 41:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: circular (ix) FEATURE:
        (A) NAME/KEY: Modified-site
        (B) LOCATION: 8
        (D) OTHER INFORMATION: /note= "Where Xaa is beta,
            beta-dimethyl cysteine"

(xi) SEQUENCE DESCRIPTION: SEQ ID NO: 41:

Cys Lys His Ala Val Val Asn Xaa
1               5

(2) INFORMATION FOR SEQ ID NO: 42:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: circular (ix) FEATURE:
        (A) NAME/KEY: Modified-site
        (B) LOCATION: 1
        (D) OTHER INFORMATION: /note= "Where Xaa is beta, beta
            tetramethylene cysteine"

(xi) SEQUENCE DESCRIPTION: SEQ ID NO: 42:

Xaa Lys His Ala Val Val Asn Cys
1               5

(2) INFORMATION FOR SEQ ID NO: 43:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: circular (ix) FEATURE:
        (A) NAME/KEY: Modified-site
        (B) LOCATION: 1
        (D) OTHER INFORMATION: /note= "Where Xaa is beta, beta
            pentamethylene cysteine"

(xi) SEQUENCE DESCRIPTION: SEQ ID NO: 43:

Xaa Lys His Ala Val Val Asn Cys
1               5

(2) INFORMATION FOR SEQ ID NO: 44:

(i) SEQUENCE CHARACTERISTICS:
        (A) LENGTH: 8 amino acids (B) TYPE: amino acid
            (C) STRANDEDNESS: <Unknown>
            (D) TOPOLOGY: circular (ix) FEATURE:
            (A) NAME/KEY: Modified-site
            (B) LOCATION: 1
            (D) OTHER INFORMATION: /note= "Where Xaa is
                beta-mercaptopropionic acid"

(xi) SEQUENCE DESCRIPTION: SEQ ID NO: 44:

Xaa Lys His Ala Val Val Asn Cys
1               5

(2) INFORMATION FOR SEQ ID NO: 45:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: circular (ix) FEATURE:
            (A) NAME/KEY: Modified-site
            (B) LOCATION: 1
            (D) OTHER INFORMATION: /note= "Where Xaa is a beta,
                beta-pentamethylene-beta-mercaptopropionic acid"

(xi) SEQUENCE DESCRIPTION: SEQ ID NO: 45:

Xaa Lys His Ala Val Val Asn Cys
1               5

(2) INFORMATION FOR SEQ ID NO: 46:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: circular (xi) SEQUENCE DESCRIPTION: SEQ ID NO: 46:

Trp Gly Gly Trp
1

(2) INFORMATION FOR SEQ ID NO: 47:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: linear (xi) SEQUENCE DESCRIPTION: SEQ ID NO: 47:

Arg Gln Ile Lys Ile Trp Phe Gln Asn Arg Arg Met Lys Trp Lys Ly
1               5                   10                  15

(2) INFORMATION FOR SEQ ID NO: 48:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: linear (xi) SEQUENCE DESCRIPTION: SEQ ID NO: 48:

Arg Gln Ile Lys Ile Trp Pro Gln Asn Arg Arg Asn Lys Trp Lys Ly
1               5                   10                  15

(2) INFORMATION FOR SEQ ID NO: 49:

(i) SEQUENCE CHARACTERISTICS:
    (A) LENGTH: 16 amino acids
    (B) TYPE: amino acid
    (C) STRANDEDNESS: <Unknown>
    (D) TOPOLOGY: linear (xi) SEQUENCE DESCRIPTION: SEQ ID NO: 49:

```
Lys Lys Trp Lys Lys Trp Trp Lys Lys Trp Trp Lys Lys Trp Lys Ly
1               5                   10                  15
```

(2) INFORMATION FOR SEQ ID NO: 50:

(i) SEQUENCE CHARACTERISTICS:
    (A) LENGTH: 22 amino acids
    (B) TYPE: amino acid
    (C) STRANDEDNESS: <Unknown>
    (D) TOPOLOGY: linear (xi) SEQUENCE DESCRIPTION: SEQ ID NO: 50:

```
Lys His Ala Val Val Asn Arg Gln Ile Lys Ile Trp Phe Gln Asn Ar
1               5                   10                  15

Arg Met Lys Trp Lys Lys
            20
```

(2) INFORMATION FOR SEQ ID NO: 51:

(i) SEQUENCE CHARACTERISTICS:
    (A) LENGTH: 8 amino acids
    (B) TYPE: amino acid
    (C) STRANDEDNESS: <Unknown>
    (D) TOPOLOGY: circular (xi) SEQUENCE DESCRIPTION: SEQ ID NO: 51:

```
Cys Lys His Gly Val Val Asn Cys
1               5
```

(2) INFORMATION FOR SEQ ID NO: 52:

(i) SEQUENCE CHARACTERISTICS:
    (A) LENGTH: 43 amino acids
    (B) TYPE: amino acid
    (C) STRANDEDNESS: <Unknown>
    (D) TOPOLOGY: linear (xi) SEQUENCE DESCRIPTION: SEQ ID NO: 52:

```
Leu Arg Ala His Ala Val Asp Ile Asn Gly Asn Gln Val Glu Asn Pr
1               5                   10                  15

Ile Asp Ile Val Ile Asn Val Ile Asp Met Asn Asp Asn Arg Pro Gl
            20                  25                  30

Phe Leu His Gln Val Trp Asn Gly Thr Val Pro
            35                  40
```

(2) INFORMATION FOR SEQ ID NO: 53:

(i) SEQUENCE CHARACTERISTICS:
    (A) LENGTH: 43 amino acids
    (B) TYPE: amino acid
    (C) STRANDEDNESS: <Unknown>
    (D) TOPOLOGY: linear (xi) SEQUENCE DESCRIPTION: SEQ ID NO: 53:

```
Leu Arg Ala His Ala Val Asp Ile Asn Gly Asn Gln Val Glu Asn Pr
1               5                   10                  15

Ile Asp Ile Val Ile Asn Val Ile Asp Met Asn Asp Asn Arg Pro Gl
            20                  25                  30
```

```
Phe Leu His Gln Val Trp Asn Gly Ser Val Pro
        35                  40
```

(2) INFORMATION FOR SEQ ID NO: 54:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 54:

```
Leu Arg Ala His Ala Val Asp Ile Asn Gly Asn Gln Val Glu Asn Pr
1               5                   10                  15
Ile Asp Ile Val Ile Asn Val Ile Asp Met Asn Asp Asn Arg Pro Gl
            20                  25                  30
Phe Leu His Gln Val Trp Asn Gly Thr Val Pro
        35                  40
```

(2) INFORMATION FOR SEQ ID NO: 55:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 55:

```
Leu Arg Ala His Ala Val Asp Val Asn Gly Asn Gln Val Glu Asn Pr
1               5                   10                  15
Ile Asp Ile Val Ile Asn Val Ile Asp Met Asn Asp Asn Arg Pro Gl
            20                  25                  30
Phe Leu His Gln Val Trp Asn Gly Thr Val Pro
        35                  40
```

(2) INFORMATION FOR SEQ ID NO: 56:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 56:

```
Leu Phe Gly His Ala Val Ser Glu Asn Gly Ala Ser Val Glu Asp Pr
1               5                   10                  15
Met Asn Ile Ser Ile Ile Val Thr Asp Gln Asn Asp His Lys Pro Ly
            20                  25                  30
Phe Thr Gln Asp Thr Phe Arg Gly Ser Val Leu
        35                  40
```

(2) INFORMATION FOR SEQ ID NO: 57:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 57:

```
Leu Tyr Gly His Ala Val Ser Glu Asn Gly Ala Ser Val Glu Glu Pr
1               5                   10                  15
Met Asn Ile Ser Ile Ile Val Thr Asp Gln Asn Asp Asn Lys Pro Ly
```

20          25          30

Phe Thr Gln Asp Thr Phe Arg Gly Ser Val Leu
            35                  40

(2) INFORMATION FOR SEQ ID NO: 58:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 58:

Leu Phe Ser His Ala Val Ser Ser Asn Gly Asn Ala Val Glu Asp Pr
1               5                   10                  15

Met Glu Ile Leu Ile Thr Val Thr Asp Gln Asn Asp Asn Lys Pro Gl
            20                  25                  30

Phe Thr Gln Glu Val Phe Lys Gly Ser Val Met
            35                  40

(2) INFORMATION FOR SEQ ID NO: 59:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 59:

Leu Leu Ser His Ala Val Ser Ala Ser Gly Gln Pro Val Glu Asp Pr
1               5                   10                  15

Met Glu Ile Ile Ile Thr Val Met Asp Gln Asn Asp Asn Lys Pro Va
            20                  25                  30

Phe Ile Lys Glu Val Phe Val Gly Tyr Ile Glu
            35                  40

(2) INFORMATION FOR SEQ ID NO: 60:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 60:

Leu Tyr Ser His Ala Val Ser Ser Asn Gly Glu Ala Val Glu Asp Pr
1               5                   10                  15

Met Glu Ile Val Ile Thr Val Thr Asp Gln Asn Asp Asn Arg Pro Gl
            20                  25                  30

Phe Thr Gln Glu Val Phe Glu Gly Ser Val Ala
            35                  40

(2) INFORMATION FOR SEQ ID NO: 61:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 61:

Leu Phe Ser His Ala Val Ser Ser Asn Gly Ala Asn Val Glu Asp Pr
1               5                   10                  15

```
Met Glu Ile Ile Ile Lys Val Gln Asp Gln Asn Asp Asn Asp Pro Va
            20                  25                  30

Phe Thr Gln Ser Val Phe Glu Gly Ser Val Pro
        35                  40
```

(2) INFORMATION FOR SEQ ID NO: 62:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 62:

```
Leu Leu Ser His Ala Val Ser Glu Asn Gly Ala Ser Val Glu Glu Pr
1               5                   10                  15

Met Glu Ile Thr Val Thr Val Ile Asp Gln Asn Asp Asn Arg Pro Ly
            20                  25                  30

Phe Thr Gln Pro Val Phe Arg Gly Ser Val Arg
        35                  40
```

(2) INFORMATION FOR SEQ ID NO: 63:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 63:

```
Leu Ser Ser His Ala Val Ser Glu Asn Gly Ser Pro Val Glu Glu Pr
1               5                   10                  15

Met Glu Ile Thr Ile Asn Val Ile Asp Gln Asn Asp Asn Arg Pro Ly
            20                  25                  30

Phe Thr Gln Asp Val Phe Arg Gly Ser Val Arg
        35                  40
```

(2) INFORMATION FOR SEQ ID NO: 64:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 64:

```
Leu Tyr Ser His Ala Val Ser Glu Asn Gly Lys Pro Val Glu Glu Pr
1               5                   10                  15

Met Glu Ile Ile Val Thr Val Thr Asp Gln Asn Asp Asn Lys Pro Gl
            20                  25                  30

Phe Thr Gln Glu Val Phe Arg Gly Ser Val Pro
        35                  40
```

(2) INFORMATION FOR SEQ ID NO: 65:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 65:

```
Leu Arg Ala His Ala Val Asp Met Asn Gly Asn Lys Val Glu Asn Pr
1               5                   10                  15
```

```
Ile Asp Leu Tyr Ile Tyr Val Ile Asp Met Asn Asp Asn Arg Pro Gl
            20                  25                  30

Phe Ile Asn Gln Val Tyr Asn Gly Ser Val Asp
        35                  40
```

(2) INFORMATION FOR SEQ ID NO: 66:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: linear (xi) SEQUENCE DESCRIPTION: SEQ ID NO: 66:

```
Met Leu Lys His Ala Val Val Asn Leu Ile Asn Tyr Gln Asp Asp Al
1               5                   10                  15

Glu Leu Ala Thr Arg Ala Ile Pro Glu Leu Ile Lys Leu Leu Asn As
            20                  25                  30

Glu Asp Gln Val Val Val Ser Gln Ala Ala Met Met
        35                  40
```

(2) INFORMATION FOR SEQ ID NO: 67:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: linear (xi) SEQUENCE DESCRIPTION: SEQ ID NO: 67:

```
Met Leu Lys His Ala Val Val Asn Leu Ile Asn Tyr Gln Asp Asp Al
1               5                   10                  15

Glu Leu Ala Thr Arg Ala Ile Pro Glu Leu Thr Lys Leu Leu Asn As
            20                  25                  30

Glu Asp Gln Val Val Val Asn Lys Ala Ala Val Met
        35                  40
```

(2) INFORMATION FOR SEQ ID NO: 68:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: linear (xi) SEQUENCE DESCRIPTION: SEQ ID NO: 68:

```
Met Leu Lys His Ala Val Val Asn Leu Ile Asn Tyr Gln Asp Asp Al
1               5                   10                  15

Glu Leu Ala Thr Arg Ala Ile Pro Glu Leu Thr Lys Leu Leu Asn As
            20                  25                  30

Glu Asp Gln Val Val Val Asn Lys Ala Ala Val Met
        35                  40
```

(2) INFORMATION FOR SEQ ID NO: 69:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: linear (xi) SEQUENCE DESCRIPTION: SEQ ID NO: 69:

```
Met Leu Lys His Ala Val Val Asn Leu Ile Asn Tyr Gln Asp Asp Al
```

```
1               5              10              15
Asp Leu Ala Thr Arg Ala Ile Pro Glu Leu Thr Lys Leu Leu Asn As
            20              25              30
Glu Asp Gln Val Val Val Ser Gln Ala Ala Met Met
        35              40
```

(2) INFORMATION FOR SEQ ID NO: 70:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: linear (xi) SEQUENCE DESCRIPTION: SEQ ID NO: 70:

```
Met Leu Lys His Ala Val Val Asn Leu Ile Asn Tyr Gln Asp Asp Al
1               5              10              15
Glu Leu Ala Thr Arg Ala Ile Pro Glu Leu Thr Lys Leu Leu Asn As
            20              25              30
Glu Asp Gln Val Val Val Asn Lys Ala Ala Val Met
        35              40
```

(2) INFORMATION FOR SEQ ID NO: 71:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: linear (xi) SEQUENCE DESCRIPTION: SEQ ID NO: 71:

```
Met Leu Lys His Ala Val Val Asn Leu Ile Asn Tyr Gln Asp Asp Al
1               5              10              15
Asp Leu Ala Thr Arg Ala Ile Pro Glu Leu Thr Lys Leu Leu Asn As
            20              25              30
Asp Asp Leu Val Val Val Asn Gln Ala Ala Val Met
        35              40
```

(2) INFORMATION FOR SEQ ID NO: 72:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (xi) SEQUENCE DESCRIPTION: SEQ ID NO: 72:

```
Asp Val Asn Glu
1
```

(2) INFORMATION FOR SEQ ID NO: 73:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: circular (xi) SEQUENCE DESCRIPTION: SEQ ID NO: 73:

```
Cys Lys Ala Val Val Cys
1               5
```